US012667631B2

(12) United States Patent
Rifkin

(10) Patent No.: US 12,667,631 B2
(45) Date of Patent: Jun. 30, 2026

(54) DISINFECTION METHOD FOR MATTRESSES AND THE LIKE

(71) Applicant: Andrew B. Rifkin, Las Vegas, NV (US)

(72) Inventor: Andrew B. Rifkin, Las Vegas, NV (US)

( * ) Notice: Subject to any disclaimer, the term of this patent is extended or adjusted under 35 U.S.C. 154(b) by 0 days.

(21) Appl. No.: 18/842,238

(22) PCT Filed: Mar. 3, 2023

(86) PCT No.: PCT/US2023/014526
§ 371 (c)(1),
(2) Date: Aug. 28, 2024

(87) PCT Pub. No.: WO2023/168092
PCT Pub. Date: Sep. 7, 2023

(65) Prior Publication Data
US 2025/0381311 A1     Dec. 18, 2025

(51) Int. Cl.
*A61L 2/202*        (2026.01)
*A47C 31/00*        (2006.01)
(Continued)

(52) U.S. Cl.
CPC .............. *A61L 2/06* (2013.01); *A47C 31/007* (2013.01); *A61L 2/202* (2013.01); (Continued)

(58) Field of Classification Search
CPC ....................................................... A61L 2/202
See application file for complete search history.

(56) References Cited

U.S. PATENT DOCUMENTS 3,736,948 A * 6/1973 Crosswhite ............... B60S 3/04
                                                      134/152
5,207,237 A * 5/1993 Langford ................ A61L 11/00
                                                      134/102.1
(Continued)

FOREIGN PATENT DOCUMENTS

DE          102019203662 A1     9/2020

*Primary Examiner* — Donald R Spamer
(74) *Attorney, Agent, or Firm* — Christopher J. Scott

(57) ABSTRACT

A disinfection system and method disinfect relatively large, unwieldy articles such as mattresses and the like. The disinfection system includes two basic components, including a barrier delivery, containment apparatus and an air treatment apparatus. The barrier delivery, containment apparatus includes at least one gas-impermeable barrier and a barrier delivery mechanism for lifting and supporting the article or mattress within the gas-impermeable barrier. The air treatment apparatus is in circulatory communication with the gas-impermeable barrier and configured to circulate apparatus-treated air through the gas-impermeable barrier for disinfecting the article or mattress as lifted and supported by the barrier delivery mechanism. The air treatment apparatus treats air by at least one of ozonating the air and heating the air during the disinfection process. The barrier delivery mechanism is collapsible and portable for easing transport of the system between applications. In some embodiments, a layered gas-impermeable barrier arrangement is provided.

18 Claims, 23 Drawing Sheets

(51) Int. Cl.
    *A61L 2/06*           (2006.01)
    *A61L 101/02*       (2006.01)
    *A61L 103/50*       (2026.01)

(52) U.S. Cl.
    CPC ....... *A61L 2101/02* (2020.08); *A61L 2103/50*
          (2026.01); *A61L 2202/11* (2013.01); *A61L*
        *2202/122* (2013.01); *A61L 2202/16* (2013.01)

(56)                 References Cited

U.S. PATENT DOCUMENTS

| | | | |
|---|---|---|---|
| 5,413,757 | A | 5/1995 | Kutner et al. |
| 6,279,589 | B1 * | 8/2001 | Goodley .............. B08B 9/0936 |
| | | | 239/722 |
| 2007/0092398 | A1 | 4/2007 | McDonald |
| 2009/0047173 | A1 * | 2/2009 | Mielnik .................. A62D 3/38 |
| | | | 422/28 |
| 2012/0164025 | A1 * | 6/2012 | Stockley, III ............. A61L 2/26 |
| | | | 422/305 |
| 2015/0166217 | A1 | 6/2015 | Deutschle et al. |
| 2023/0211032 | A1 * | 7/2023 | Suh ........................... A61L 2/24 |

\* cited by examiner

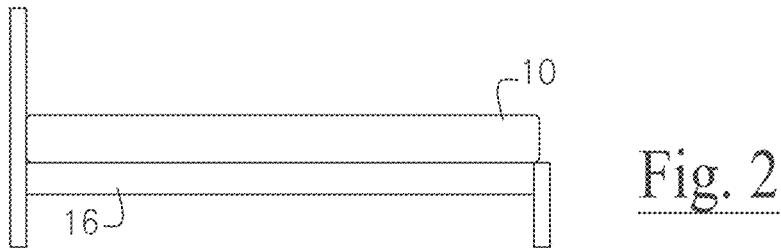
_Fig. 2_
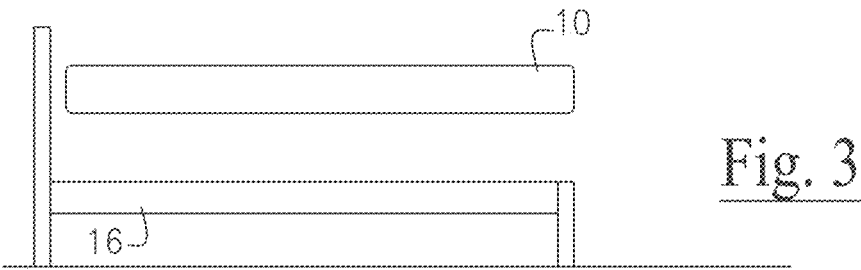
_Fig. 3_
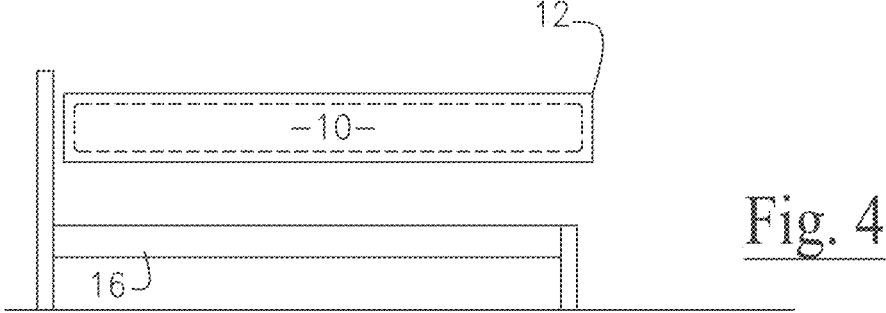
_Fig. 4_
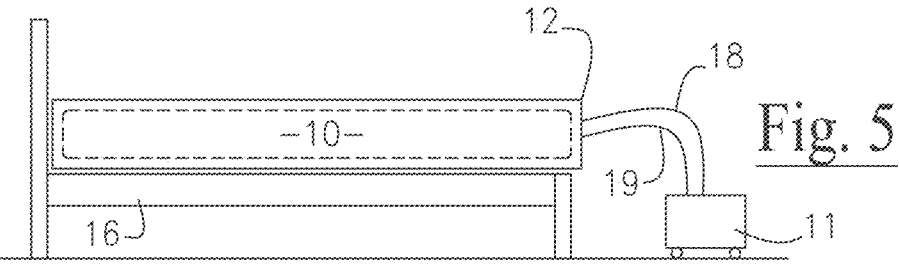
_Fig. 5_

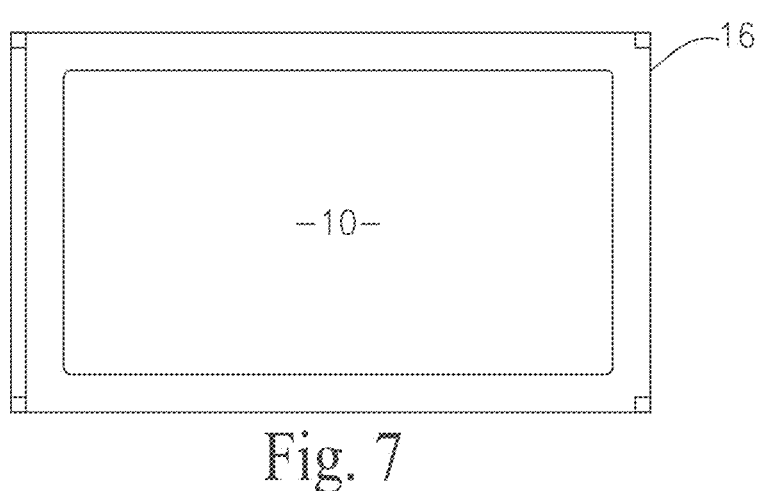
Fig. 7
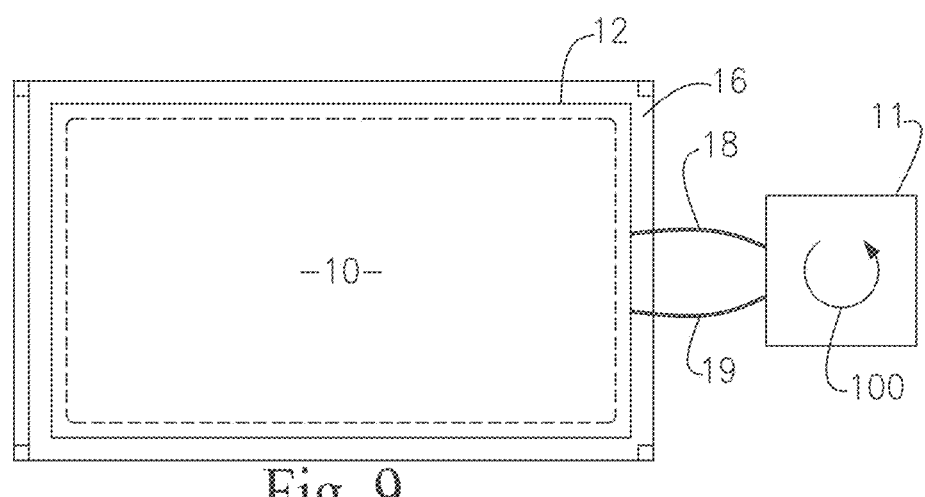
Fig. 8
Fig. 9

DISINFECTION METHOD FOR MATTRESSES AND THE LIKE

FIELD OF THE INVENTION

The present invention generally relates to a system and method for disinfecting mattresses and the like. More particularly, the present invention relates to a system for disinfecting relatively large articles as exemplified by a mattress and provides a barrier delivery containment apparatus for installing a gas-impermeable barrier around the relatively large articles in circulatory communication with an air treatment apparatus for cycling heated or ozonated apparatus-treated air within the gas-impermeable barrier for disinfecting articles received therein.

BRIEF DESCRIPTION OF THE PRIOR ART

US Patent Application Publication No. 2022/0249718 ('718 Publication), authored by Rifkin, discloses a Compact Ultraviolet Light Source Apparatus. The '718 Publication describes a compact, portable, low cost ultraviolet (UV) light source apparatus that irradiates select or target surfacing for disinfecting or sanitizing the target surfacing or for decomposing ozone within a defined ozone environment. The ultraviolet light source apparatus essentially includes a power source; an ultraviolet (UV) light source in communication with the power source, and a mechanism for powering on and powering off the ultraviolet (UV) light source.

The ultraviolet (UV) light source directs ultraviolet light toward a select surface for irradiating the surface or decomposing ozone. The object-sanitizing assembly may thus be said to essentially comprise a power source, an ultraviolet (UV) light source in communication with the power source, an ozone source in communication with the power source, and means for powering on and powering off (a) the ultraviolet light source and (b) the ozone source. The ozone source is configured to direct ozone into and circulate ozone within the object-holding container for sanitizing objects received and held within the object-holding container. The ultraviolet (UV) light source or matrices are configured to direct ultraviolet (UV) light into the object-holding container after ozone sanitization for decomposing ozone within the object-holding container. The ultraviolet (UV) light source apparatus may be attached to any number of select surfaces or objects or may be utilized to receive and hold objects for treating surfacing thereof.

The presently disclosed subject matter builds upon the concepts set forth and described in the '718 Publication and addresses the need to disinfect relatively larger articles in an era characterized in part by higher sensitivity to cleaner accommodations, and particularly mattresses in either residential or commercial accommodation application scenarios. Viruses exemplified by Covid-19, bed bugs, and bacteria live and breed in hotel rooms. Currently there are no simple, safe and efficient options to ensure a hotel room is truly clean. The presently disclosed subject matter provides an innovate disinfection system and process that sanitizes mattresses removing viruses, bed bugs, odors, and bacteria in less time than it takes to perform a standard room clean.

The presently disclosed subject matter can be applied to bedding, blankets, pillows, and furniture cushions. The rapid, easy to use disinfection solution according to the presently disclosed subject matter is sustainable, non-toxic, and chemical-free. In this last regard, the disinfection solution according to the presently disclosed subject matter is easy to use by a single operator and does not prevent other room cleaning processes to be performed while the disinfection system is cycling and underway. There is no requirement to remove mattresses from a room during the disinfection process. The result is a faster complete sanitation process that takes under 30 minutes to complete. The mattress is rapidly and safely disinfected during the normal room cleaning and disinfection checkout schedules. Further, mattress life is extended by eliminating the need for airtight mattress covers which typically reduce mattress life expectancy. The prior art thus perceives a need for a system and method for disinfecting mattresses and the like incorporating a barrier delivery containment apparatus and a disinfection generator as summarized in more detail hereinafter.

SUMMARY OF THE INVENTION

There is thus provided in accordance with an embodiment of the presently disclosed subject matter a disinfection system for disinfecting an article exemplified by a mattress. The disinfection system comprises, in combination a barrier delivery, containment apparatus and an air treatment apparatus or disinfection generator. The barrier delivery, containment apparatus comprises at least one gas-impermeable barrier and a barrier delivery mechanism for lifting and supporting the article within the at least one gas-impermeable barrier. Once the mattress is fully encapsulated or enveloped by the gas-impermeable barrier, the air treatment apparatus or disinfection generator, in communication with a power source, is attached or connected to the gas-impermeable barrier and configured to continually circulate apparatus-treated air through the gas-impermeable barrier arrangement for disinfecting the article or mattress as lifted and supported therewithin. When the disinfection cycle is finished, the air treatment apparatus is disconnected from the gas-impermeable barrier and the integrated barrier delivery containment apparatus is removed from the mattress, and collapsed for enhanced transportability to a successive application.

In some embodiments, the gas-impermeable barrier comprises a barrier length, a barrier width, and a barrier height. The barrier length, the barrier width, and the barrier height are respectively greater than an article length, an article width, and an article height so as to fully envelope or encapsulate the target article or mattress. The barrier delivery mechanism is configured to maximize an internal volume of the gas-impermeable barrier for enhancing circulation of the apparatus-treated air therewithin. In some embodiments, the article or mattress may be supported by a support structure as exemplified by either a box spring or bed frame. The barrier delivery mechanism comprises a front end, a rear end, and a series of rollers intermediate the front and rear ends. The front end is insertable intermediate the article and the support structure for elevating the article relative to the support structure. The series of rollers enable the article to roll thereatop, and the gas-impermeable barrier envelopes the series of rollers and the article while the apparatus-treated air circulates within the at least one gas-impermeable barrier.

In some embodiments, the barrier delivery, containment apparatus is height adjustable to accommodate differences in height of the support structure. In some embodiments, the barrier delivery mechanism comprises a wedge-shaped lead element. The wedge-shaped lead element wedges intermediate the article or mattress and the support structure as the barrier delivery mechanism envelopes the article or mattress within the gas-impermeable barrier. In some embodiments, the barrier delivery, containment apparatus is collapsible and portable. In some embodiments, the barrier delivery, containment apparatus may be provided in either a collapsible accordion style foldable unit or may, in certain embodiments, comprises a vertical stowage configuration and a horizontal application configuration. In these latter embodiments, the barrier delivery mechanism is retractable into the vertical stowage configuration for portability of the disinfection system transportable as a single unit upon a carriage assembly. In these latter embodiments, the front end of the barrier delivery mechanism is configured for ready-insertion intermediate the article and the support structure when the barrier delivery mechanism is retracted into the vertical stowage configuration. In other words, once the barrier delivery mechanism is retracted, the lead element is positioned for successive applications.

In some embodiments, the barrier delivery, containment apparatus comprises a series of gas-impermeable barriers including an interior bottom bladder barrier, an interior top bladder barrier, and an exterior over-barrier. The interior bottom bladder barrier and the interior top bladder barrier direct apparatus-treated air against article or mattress surfacing. The exterior over-barrier envelopes the interior bottom bladder barrier and the interior top bladder barrier and directs exhausting apparatus-treated air back to the air treatment apparatus for supplemental ozone and/or heat and for capturing contaminants that are collected during the disinfection cycle. In some embodiments, the interior bottom bladder barrier and the interior top bladder barrier each comprise article-opposing surfacing, which article-opposing surfacing comprises a series of apertures for more directly directing apparatus-treated air against article or mattress surfacing during the disinfection cycle.

There is further provided in accordance with another aspect of the presently disclosed subject matter a disinfection method for disinfecting an article or mattress. The disinfection method according to the presently disclosed subject matter comprises the steps of positioning a barrier delivery, containment apparatus at a first end of an article or mattress. The integrated barrier delivery, containment apparatus comprises at least one gas-impermeable barrier and a barrier delivery mechanism. The barrier delivery mechanism is then directed toward the article or mattress thereby simultaneously supporting and enveloping the article within the gas-impermeable barrier. The powered air treatment apparatus or disinfection generator is placed into circulatory communication with the gas-impermeable barrier and apparatus-treated air is then continuously circulated through the gas-impermeable barrier for an interval of time controlled by the operator.

In some embodiments, the method comprises the step of firstly supporting the article or mattress with a support structure in elevated relation to a ground surface. The barrier delivery mechanism comprises a front end, a rear end, and a series of rollers intermediate the front and rear ends. The front end is insertable intermediate the article or mattress and the support structure when the barrier delivery mechanism is directed toward the article for elevating the article relative to the support structure. The series of rollers enable the article to roll thereatop. The gas-impermeable barrier envelopes or encapsulates the series of rollers and the mattress while apparatus-treated air circulates within the at least one gas-impermeable barrier. In some embodiments, the method comprises the step of adjusting a height of the front end and rear end such that the front end is readily insertable intermediate the mattress and the mattress support structure when the barrier delivery mechanism is directed theretoward.

In some embodiments, the barrier delivery mechanism comprises a wedge-shaped lead element at the front end, which wedge-shaped lead element wedges intermediate the article or mattress and the mattress support structure as the barrier delivery mechanism envelopes the article within the gas-impermeable barrier. In some embodiments, the method comprises the steps of collapsing and transporting the barrier delivery, containment apparatus after the apparatus has been reconfigured into a stowage, portable configuration. In some embodiments, the barrier delivery, containment apparatus comprises a vertical stowage configuration and a horizontal application configuration. In these latter embodiments, the barrier delivery mechanism is retractable into the vertical stowage configuration for easing or enhancing portability of the barrier delivery, containment apparatus. In some embodiments, the front end of the barrier delivery mechanism is configured for ready insertion intermediate the article and the support structure when the barrier delivery mechanism is fully retracted into the vertical stowage configuration.

In some embodiments, the barrier delivery, containment apparatus comprises a series of layered gas-impermeable barriers including an interior bottom bladder barrier, an interior top bladder barrier, and an exterior over-barrier. The interior bottom bladder barrier and the interior top bladder barrier direct apparatus-treated air against article or mattress surfacing of the article or mattress. The exterior over-barrier envelopes the interior bottom bladder barrier and the interior top bladder barrier and directs exhausting apparatus-treated air back to the air treatment apparatus. In some embodiments, the interior bottom bladder barrier and the interior top bladder barrier each comprise article-opposing surfacing. The article-opposing surfacing comprises a series of apertures for aperture-directing apparatus-treated air against the article surfacing.

In some embodiments, the air treatment apparatus otherwise referred to as a converter unit or disinfection generator, treats air by at least one of ozonating the air and heating the air during air treatment and the article disinfection process. In some embodiments, the article disinfection system and method disinfect the article or mattress by way of ozonated air as ozonated by the air treatment apparatus or disinfection generator. In some embodiments, the apparatus-treated air is ozonated to a minimum of 2 ppm to 4 ppm depending on the targeted material or surface application. In some embodiments, the article disinfection system and method disinfect the article or mattress by way of heated air as heated by one or more heaters incorporated into the air treatment apparatus. In some embodiments, the apparatus-treated air is heated to and maintained at a temperature range, the temperature range being from 110 to 120 degrees Fahrenheit. The disinfection system according to the presently disclosed subject matter treats air by at least one of ozonating the air and heating the air.

In some embodiments, the barrier delivery mechanism comprises a barrier mouth at the front end. The barrier mouth may comprise an arcuate upper frame portion, the arcuate upper frame portion for elevating a front portion of the gas-impermeable barrier as the barrier delivery apparatus envelopes the article in some embodiments. In some embodiments, the gas-impermeable barrier comprises an open barrier front end, which open barrier front end receives the article as the barrier delivery apparatus envelopes the article with the gas-impermeable barrier. In some embodiments, the open barrier front end comprises a closure mechanism exemplified by a zipper mechanism or matable hook and loop fastening arrangements for enabling a user to selectively close the gas-impermeable barrier once the article or mattress is fully enveloped by the gas-impermeable barrier.

BRIEF DESCRIPTIONS OF THE DRAWINGS

Other features of the invention will become more evident from a consideration of the following brief descriptions of patent drawings:

FIG. 2 is a first sequential diagrammatic lateral view depiction of a basic bed assembly including a mattress supported by a mattress support frame.

FIG. 3 is a second sequential diagrammatic lateral view depiction of a basic bed assembly with a mattress elevated relative to a mattress support frame.

FIG. 4 is a third sequential diagrammatic lateral view depiction of a mattress elevated relative to a mattress support frame and enveloped by a gas-impermeable barrier.

FIG. 5 is a fourth sequential diagrammatic lateral view depiction of a mattress enveloped in a gas-impermeable barrier and supported by a mattress support frame with an air treatment apparatus in circulatory communication with the gas-impermeable barrier for circulating apparatus-treated air through the gas-impermeable barrier.

FIG. 7 is a first sequential diagrammatic top view depiction of a basic bed assembly including a mattress supported by a mattress support frame.

FIG. 8 is a second sequential diagrammatic top view depiction of a basic bed assembly with a mattress enveloped in a gas-impermeable barrier atop the mattress support frame.

FIG. 9 is a third sequential diagrammatic top view depiction of a mattress enveloped in a gas-impermeable barrier and supported by a mattress support frame with an air treatment apparatus in circulatory communication with the gas-impermeable barrier for circulating apparatus-treated air through the gas-impermeable barrier.

DETAILED DESCRIPTIONS OF THE EMBODIMENTS

The presently disclosed subject matter generally concerns a system and method for disinfecting a mattress 10 and similar other articles that builds upon the concepts described in US Patent Application Publication No. 2022/0249718 ('718 Publication) authored by Rifkin. As introduced in the '718 Publication, ozone is a powerful oxidant and virucide. Ozone is produced when oxygen ($O_2$) molecules are dissociated by an energy source into oxygen atoms and subsequently collide with an oxygen molecule to form an unstable gas, ozone ($O_3$), which is used to disinfect ambient environments. Most ozone is generated by imposing a high voltage alternating current across a dielectric discharge gap that contains an oxygen-bearing gas. Ozone is often generated onsite of a target disinfection space because it is unstable and decomposes to elemental oxygen in a short amount of time after generation.

The mechanisms of disinfection using ozone typically include (a) direct oxidation/destruction of the cell wall with leakage of cellular constituents outside of the cell; (b) reactions with radical by-products of ozone decomposition; (c) damage to the constituents of the nucleic acids (purines and pyrimidines); and (d) breakage of carbon-nitrogen bonds leading to depolymerization. It is generally believed that bacteria are destroyed because of protoplasmic oxidation resulting in cell wall disintegration (cell lysis). The effectiveness of disinfection depends on the susceptibility of the target organisms, the contact time, and the concentration of the ozone. The components of an ozone disinfection system include feed-gas preparation, ozone generation, ozone contacting, and ozone destruction. Air or pure oxygen is typically used as the feed-gas source and is passed to the ozone generator at a set flow rate. The energy source for production is generated by electrical discharge in a gas that contains oxygen.

Figure 1:
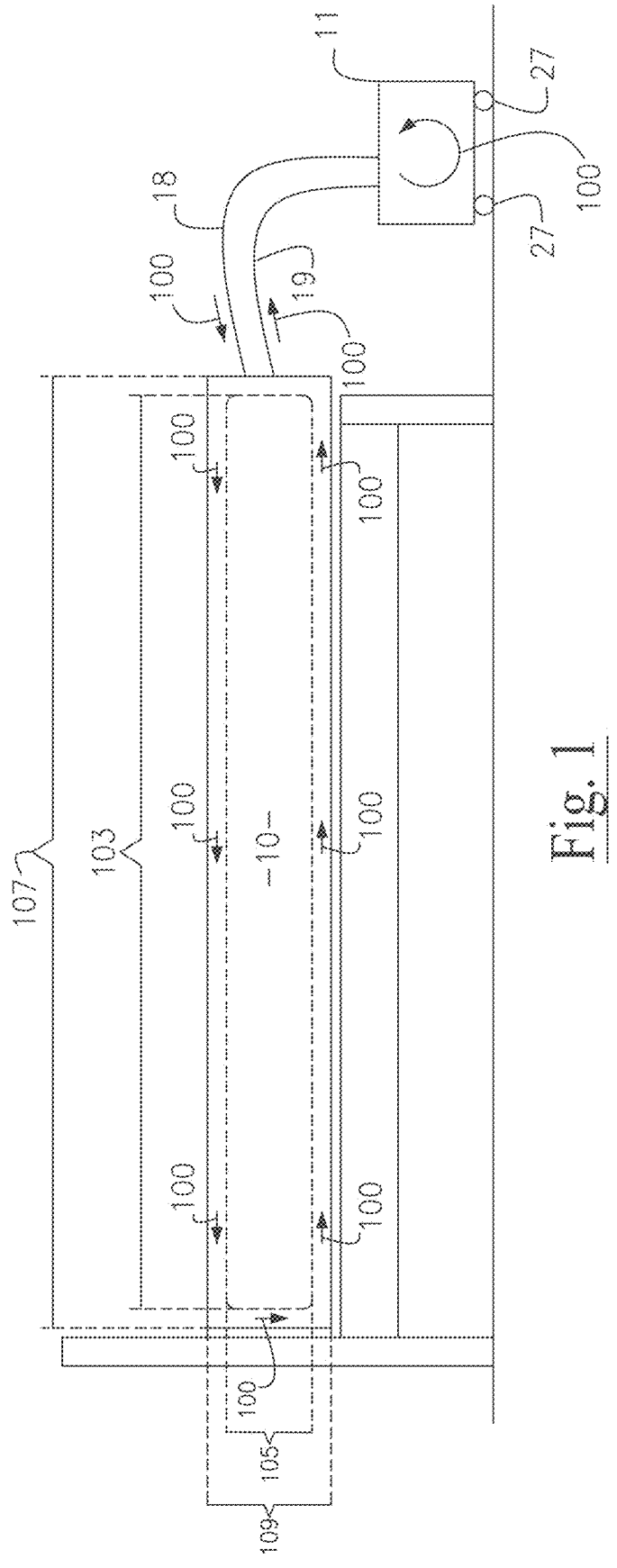
FIG. 1 is a diagrammatic lateral view depiction of basic disinfection system components according to the presently disclosed subject matter including a basic bed assembly and a gas-impermeable barrier enveloping a mattress of basic bed assembly with an air treatment apparatus in circulatory communication with the gas-impermeable barrier for circulating apparatus-treated air therethrough.
Figure 6:
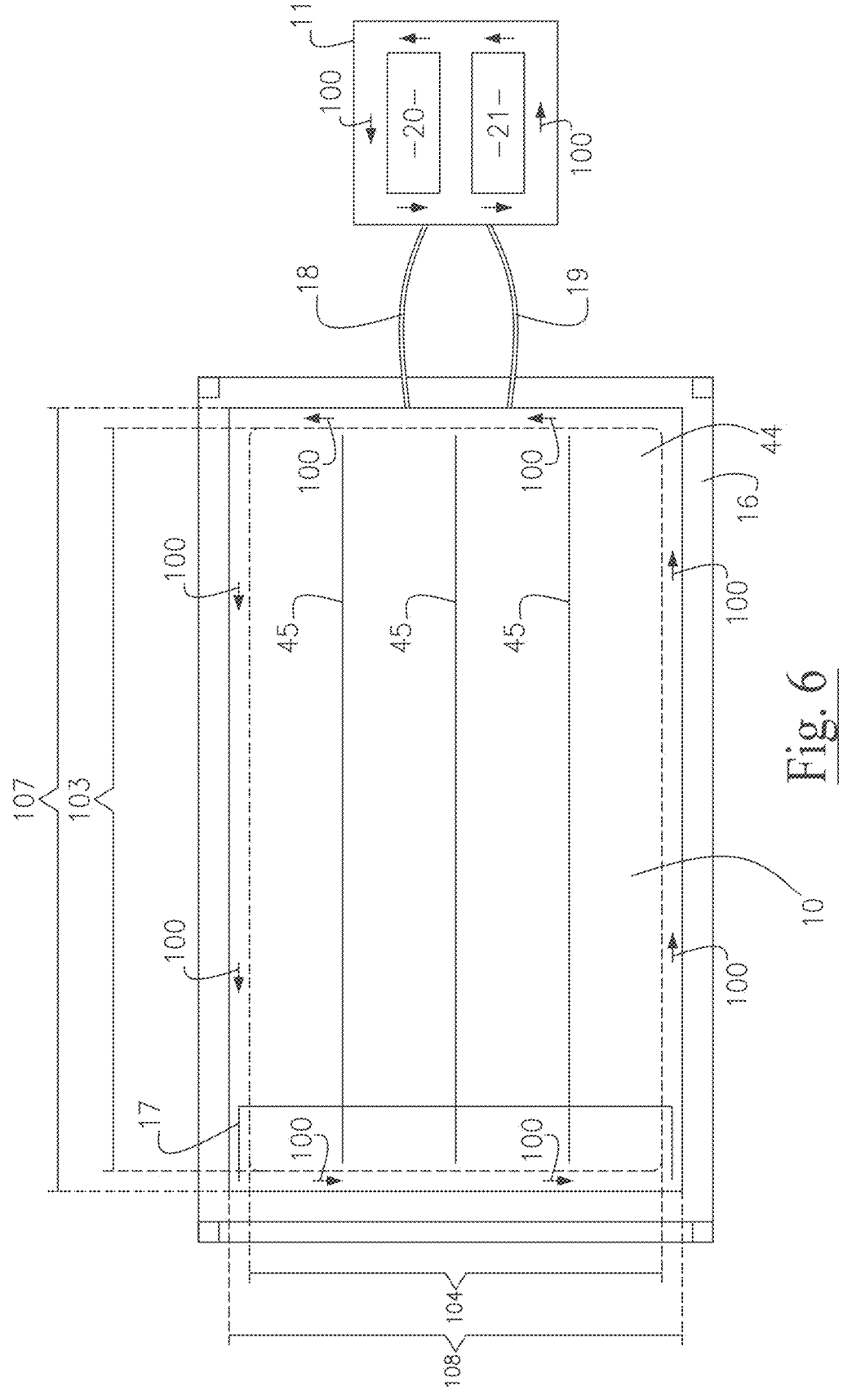
FIG. 6 is a diagrammatic top view depiction of the basic disinfection system components according to the presently disclosed subject matter including a basic bed assembly with a gas-impermeable barrier enveloping a mattress with an air treatment apparatus in circulatory communication with the gas-impermeable barrier for circulating apparatus-treated air therethrough.

The disinfection system according to the presently disclosed subject matter comprises a converter unit, disinfection generator, or air treatment apparatus as at 11, which converter unit, disinfection generator or air treatment apparatus 11 comprises at least one mechanism for generating ozone or at least one ozone generator as at 20 and at least one mechanism for heating ozonated air or one or more heaters as at 21. Together the at least one ozone generator 20 and the at least one heater 21 selectively provide either ozonated apparatus-treated air or heated apparatus-treated air that is sourced by the converter unit, disinfection generator or air treatment apparatus 11 for delivery to a volumetric space defined by at least one gas-impermeable barrier 12 that encases, encapsulates, or envelopes a target mattress 10 or similar other article as generally and diagrammatically depicted in FIG. 1. Generally, the apparatus-treated air is either ozonated or heated depending on the application. Ozonated apparatus-treated air is circulated through the gas-impermeable barrier 12 to kill bacteria, viruses, and the like. Heated apparatus-treated air is circulated through the gas-impermeable barrier 12 to rapidly destroy ozone as needed, and to kill parasites such as bed bugs, hair lice, dust mites, etc. The disinfection system according to the presently disclosed subject matter treats air by at least one of ozonating the air and heating the air.

In some embodiments, the air treatment apparatus 11 may preferably comprise a series of heater units to maintain a desired temperature of the heated apparatus-treated air. The preferred operating temperature of the heated apparatus-treated air according to the presently disclosed disinfection system is on the order of 110 to 120 degrees Fahrenheit introduced in line with the ozone recirculation system in some embodiments. The ozone generator 20 is preferably provided to produce ozonated air from ambient air. The ozone level is preferably and controllably measured so that a minimum of 2 parts per million to 4 parts per million or 2 ppm to 4 ppm are provided in the circulating ozonated apparatus-treated air depending on the targeted material or surface application. The converter unit/air treatment apparatus 11 may be provided as a separate portable unit as generally depicted in FIGS. 1, 5, 6, 9, 18, 20, and 22, or installed on a single transportable apparatus delivery carriage 30 as generally depicted in FIGS. 23-26.

In some embodiments, a barrier delivery, containment apparatus as at 13 allows or enables a single person to lift a (hotel) mattress 10 off of a first support platform or structure as exemplified by a box spring as at 15 or a bed frame as at 16. The barrier delivery, containment apparatus 13 further supports the mattress 10 upon a second support platform provided by a series of mattress support rollers 23 of the barrier delivery, containment apparatus 13 simultaneously enclosing or encasing the mattress 10 in a gas-impermeable envelope, wrapper or barrier as at 12. The presently disclosed subject matter further contemplates certain means for allowing or enabling a user to enclose other objects such as blankets, pillows, sofa cushions, etc. in the gas-impermeable barrier 12.

An inlet line/hose 18 and an outlet line/hose 19 are connected to the gas-impermeable barrier 12 and the converter unit/air treatment apparatus 11 for circulating (as at arrows 100) heated apparatus-treated air or ozonated apparatus-treated air within the gas-impermeable barrier 12 as generated or generated by the converter unit or air treatment apparatus 11. The heated or ozonated apparatus-treated air is introduced into the gas-impermeable barrier 12 via the inlet line/hose 18 which heated or ozonated apparatus-treated air permeates the volumetric space within the gas-impermeable barrier 12 to disinfect/sanitize the mattress 10 by killing or inactivating bacteria, viruses, parasites (e.g. bed bugs), and pests and removing odors. The heated or ozonated ambient air environment within the gas-impermeable barrier 12 is then exhausted back to the converter unit or air treatment apparatus 11 via the outlet line/hose 19 where bacteria, viruses, parasites, and pests may be collected for disposal.

In some embodiments, the convertor unit or air treatment apparatus 11 may preferably comprise a series of blower motors and blowers. The series of blower motors and blowers help inject the heated or ozonated apparatus-treated air or into the gas-impermeable barrier 12 and return the heated or ozonated apparatus-treated air back to the convertor unit or air treatment apparatus 11. In some embodiments, additional blower motors may be provided to ensure sufficient heated or ozonated air distribution within the gas-impermeable barrier 12. Additional blower motors may be further provided for inflating a series of layered gas-impermeable barriers or a layered gas-impermeable barrier arrangement with heated or ozonated apparatus-treated air as sourced by the converter unit or air treatment apparatus 11 and returning the exhausting heated or ozonated apparatus-treated air from the layered gas-impermeable barrier arrangement to the converter unit or air treatment apparatus 11 in some embodiments.

The convertor unit or air treatment apparatus 11 may further comprise a HEPA filter in communication with the outlet line/hose 19 to trap any foreign materials or debris that may have been picked up during the air return process. In some embodiments, the convertor unit or air treatment apparatus 11 is made operable by way of an AC line voltage of 110v or 220v. The convertor unit or air treatment apparatus 11 may further preferably comprise a microcontroller for controlling both temperature measurement and regulation and ozone measurement and regulation including process flow and safety monitoring for pressure leaks, temperature issues, etc. As prefaced above, the ozone level is preferably controllably measured so that a minimum of 2 parts per million to 4 parts per million or 2 ppm to 4 ppm are provided in the circulating ozonated apparatus-treated air depending on the target material or surface application.

In some embodiments, the barrier delivery, containment apparatus 13 is collapsible and portable for easing transportability between rooms as in hotel bedroom application scenarios. The collapsible, portable barrier delivery, containment apparatus 13 may be operated by a single operator, and is configured so as to not require that the mattress 10 be removed from the box spring 15 or bed frame 16. The barrier delivery, containment apparatus 13 can be further configured into 3 or 4 sections for easy insertion in limited space between the foot end of a mattress 10 and opposing furniture or wall.

Figures 10, 11:
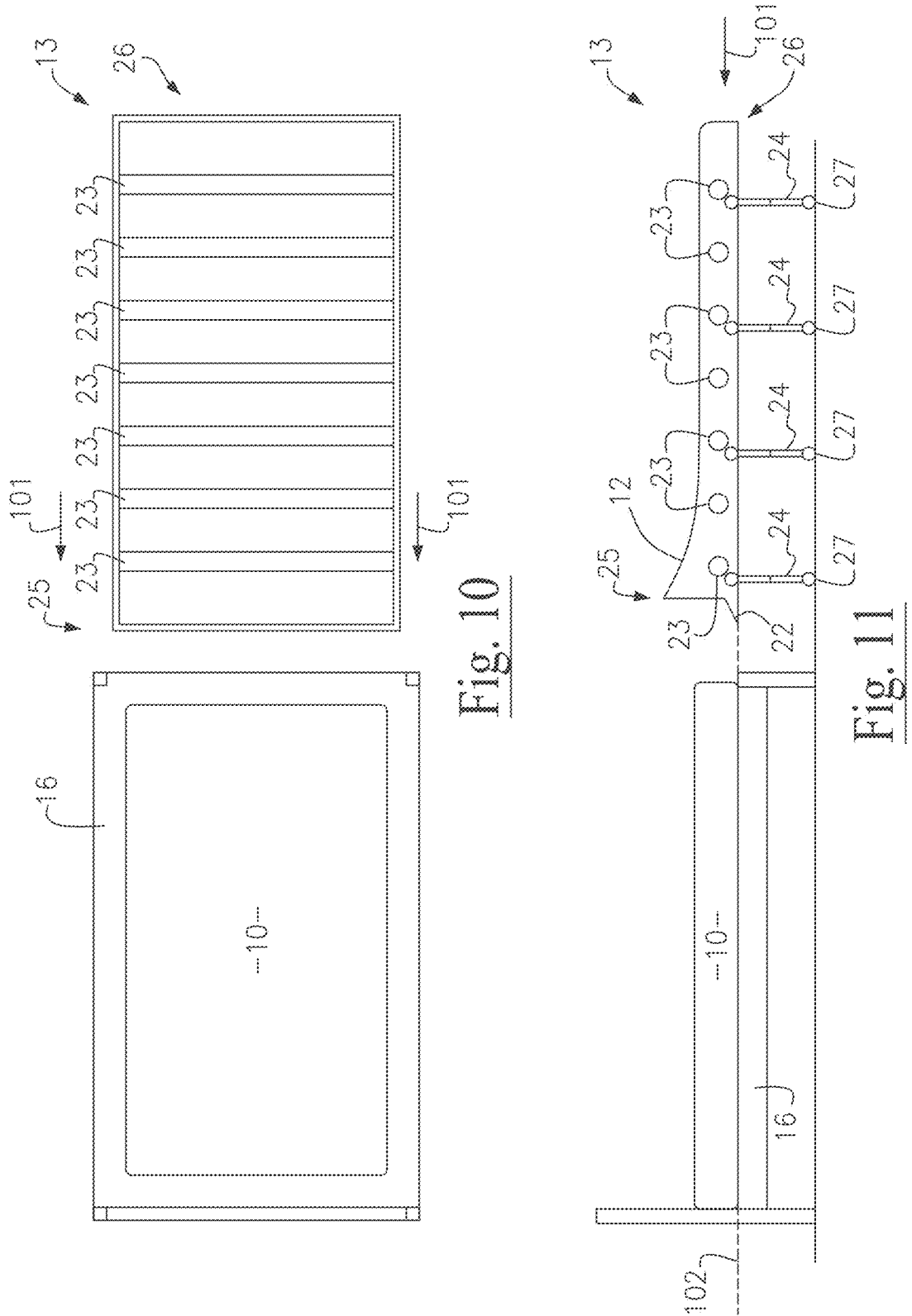
FIG. 10 is a diagrammatic top view depiction of a basic bed assembly with a mattress supported by a mattress support frame and a basic barrier delivery mechanism positioned at a first end of the basic bed assembly and being directed toward the basic bed assembly.
FIG. 11 is a diagrammatic lateral view depiction of a basic bed assembly with a mattress supported by a mattress support frame and a basic barrier delivery mechanism positioned at a first end of the basic bed assembly and being directed toward the basic bed assembly.
Figures 12, 13:
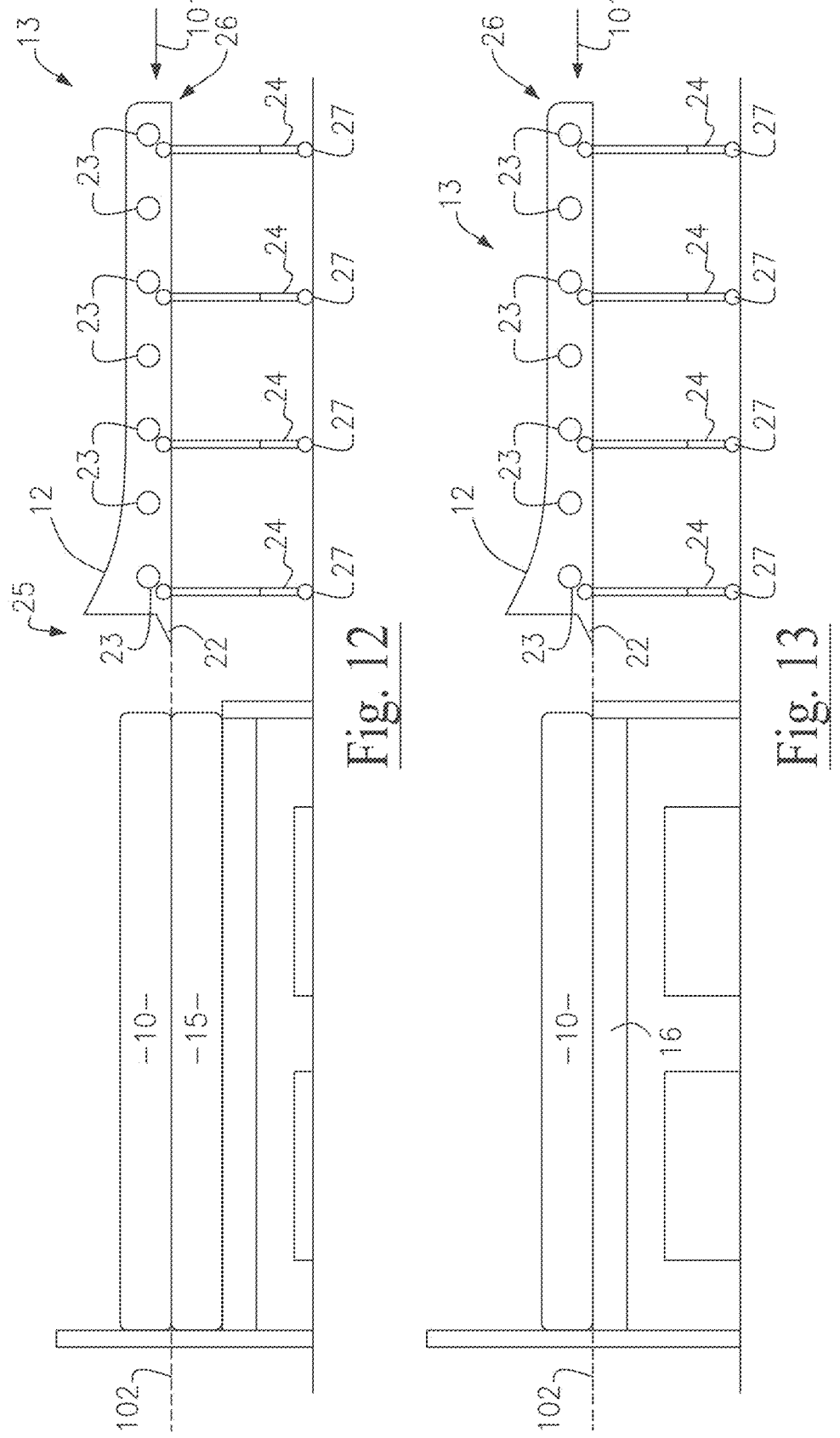
FIG. 12 is a diagrammatic lateral view depiction of a basic bed assembly with a mattress supported by a box spring and a mattress support frame and a height adjusted basic barrier delivery mechanism positioned at a first end of the basic bed assembly and being directed toward the basic bed assembly.
FIG. 13 is a diagrammatic lateral view depiction of a basic bed assembly with a mattress supported by an elevated mattress support frame and a height adjusted basic barrier delivery mechanism positioned at a first end of the basic bed assembly and being directed toward the basic bed assembly.

The height of the barrier delivery, containment apparatus 13 can be easily adjusted higher or lower to accommodate differences in height between the first support platform (e.g. box spring 15 or bed frame 16) and the bottom surface of the mattress 10. Comparatively referencing FIGS. 11-13, for example, it will be seen the barrier delivery, containment apparatus 13 may comprise a series of expandable or telescopic legs 24 outfitted with caster wheels 27, which telescopic legs 24 may be selectively extended to raise or lower the barrier delivery, containment apparatus 13 as needed to position the front end 25 of the barrier delivery, containment apparatus 13 at an insertion plane 102 intermediate the bottom of the mattress 10 and the underlying support structure as exemplified by a box spring 15 or bed frame 16.

The barrier delivery, containment apparatus 13 may be unfolded by the operator and the front end 25 of the barrier delivery, containment apparatus 13 may comprise a large, angled surface or wedge-shaped lead element 22. In some embodiments, the wedge-shaped lead element 22 has an element length 110 at least equal to a roller length 111 of each mattress support roller 23 as particularly referenced in FIG. 27 and as further generally depicted in FIGS. 23 and 24. The angled forward/front surface or wedge-shaped lead element 22 is operable to lift the mattress 10 as the barrier delivery, containment apparatus 13 is directed as at arrows 101 into engagement with the mattress 10 while the bottom of the mattress 10 easily rolls atop the series of mattress support rollers 23 of the barrier delivery, containment apparatus 13. The series of mattress support rollers 23 provide low friction surfacing insertable intermediate the mattress 10 and underlying first support platform exemplified by a box spring 15 or bed frame 16 sufficiently raising the mattress 10 for encasement in the gas-impermeable barrier 12 while supporting the mattress 10 and thereby providing a second support platform for mattress disinfection. The barrier delivery, containment apparatus 13 is configured to deploy the gas-impermeable barrier 12 automatically encasing the mattress 10 in the gas-impermeable barrier 12 as the series of mattress support rollers 23 are inserted between the mattress 10 and the underlying support structure. Once the gas-impermeable barrier 12 is fully enveloped around the mattress 10, the open (front) end 25 is preferably zippered closed by way of a zipper mechanism as at 17 or similar other closure mechanism (e.g. matable hook and loop fastening means).

The mattress 10 can be easily moved once supported by the mattress support rollers 23 of the barrier delivery, containment apparatus 13, and can be pulled forward or rearward to help facilitate closure of the gas-impermeable barrier 12 by way of the closure mechanism or zipper mechanism 17 despite close proximity to peripheral objects (e.g. night tables) that may block access to the bag closure and zipper mechanism 17. In other words, the mattress support rollers 23 in the framing support under the mattress 10 also serve as a method to pull forward or rearward the mattress 10 with the gas-impermeable barrier 12 enclosing the mattress. By providing this roller system, the mattress 10 may be displaced to and fro and such that the mattress 10 may be moved away from a wall or headboard and any furniture that is engaged on the side of the mattress 10 such as night tables. The mattress support rollers 23 give the user much easier access to close the gas-impermeable barrier 12 at the open end, since the mattress 10, as enclosed in the gas-impermeable barrier can be moved away from the wall, headboard or interfering furniture.

Figures 14, 15:
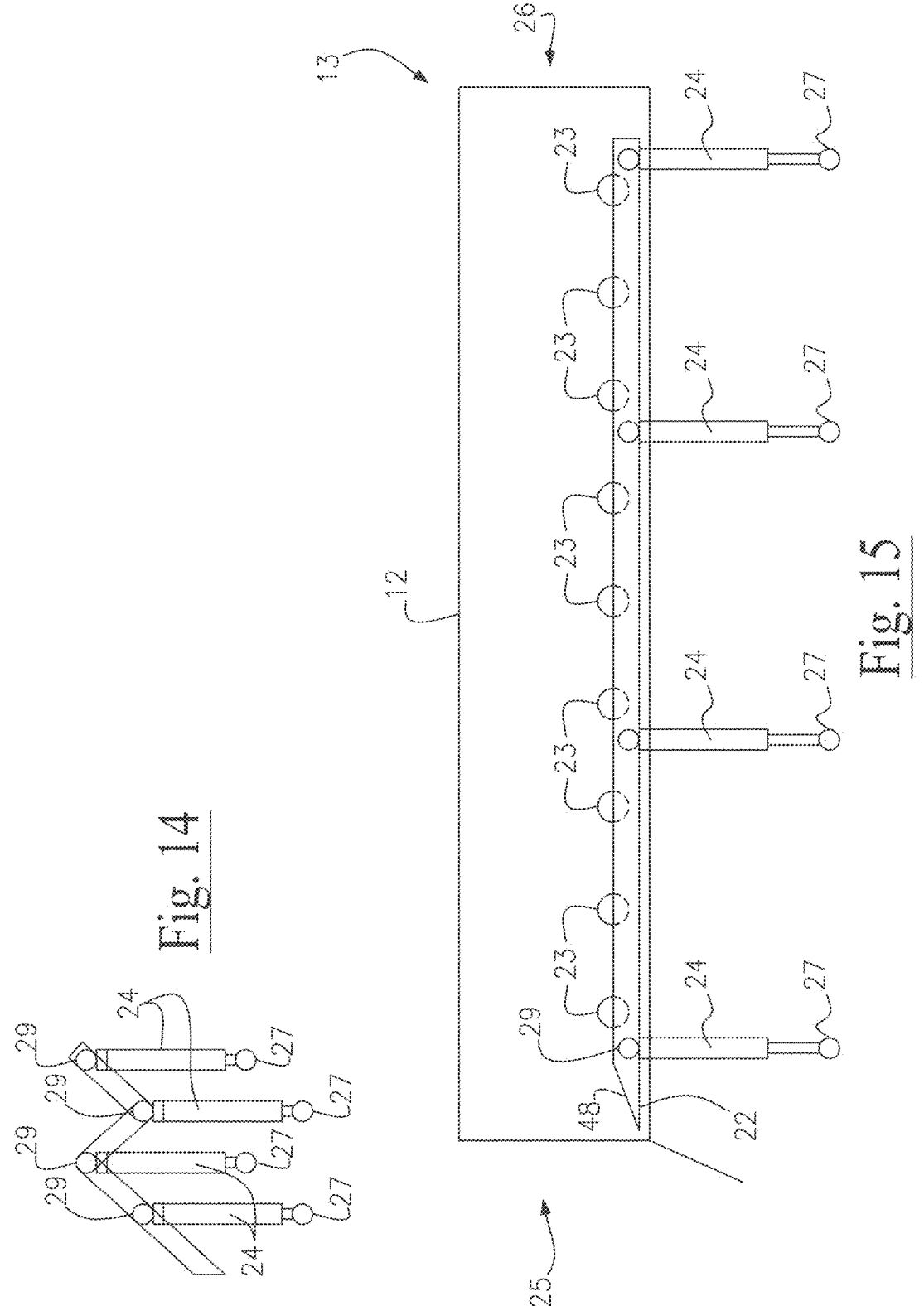
FIG. 14 is a diagrammatic depiction of a basic barrier delivery mechanism according to the presently disclosed subject matter shown collapsed into an accordion stye collapsed configuration.
FIG. 15 is a diagrammatic lateral view depiction of a first alternative barrier delivery, containment apparatus according to the presently disclosed subject matter showing a series of mattress support rollers supported by a series of height adjustable legs and an open-ended gas-impermeable barrier encapsulating the series of mattress support rollers.
Figure 16:
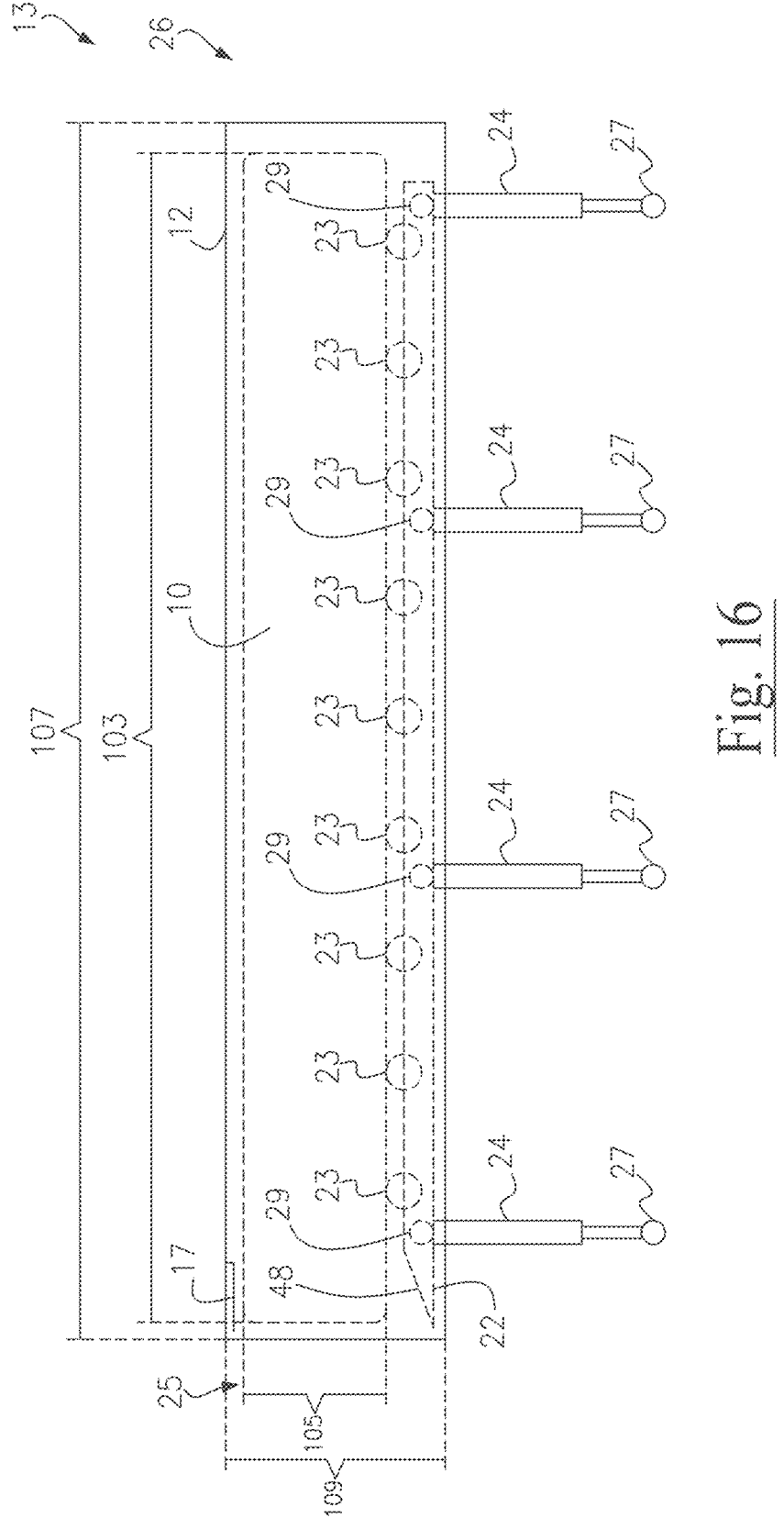
FIG. 16 is a diagrammatic lateral view depiction of the first alternative barrier delivery, containment apparatus according to the presently disclosed subject matter showing a series of mattress support rollers supported by a series of height adjustable legs and a gas-impermeable barrier enveloping a mattress as supported atop the series of mattress support rollers.
Figure 17:
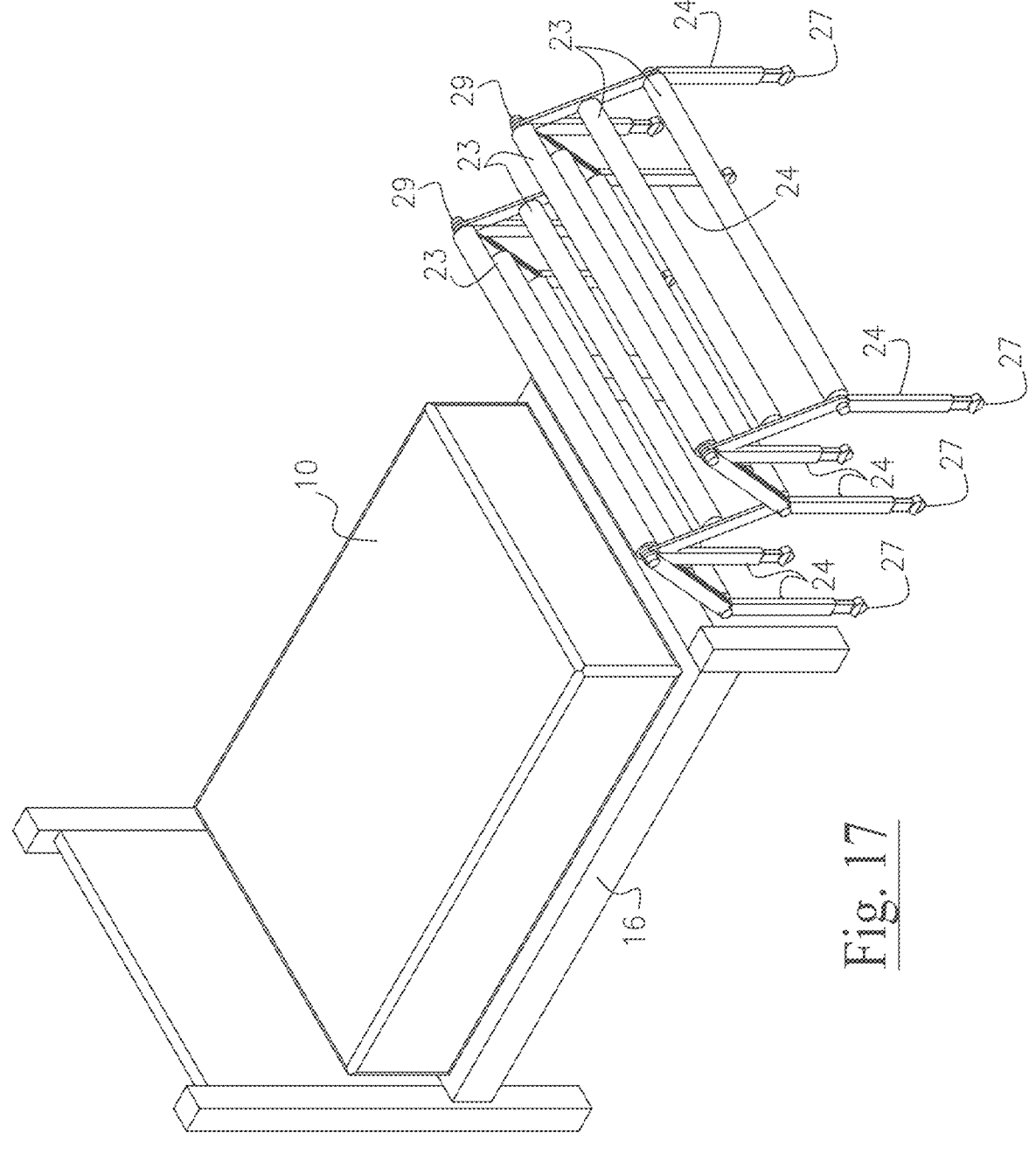
FIG. 17 is a top perspective depiction of a basic bed assembly with a mattress supported by an elevated mattress support frame and a first alternative barrier delivery mechanism positioned at a first end of the basic bed assembly shown partially collapsed in an accordion stye collapsed configuration.
Figure 18:
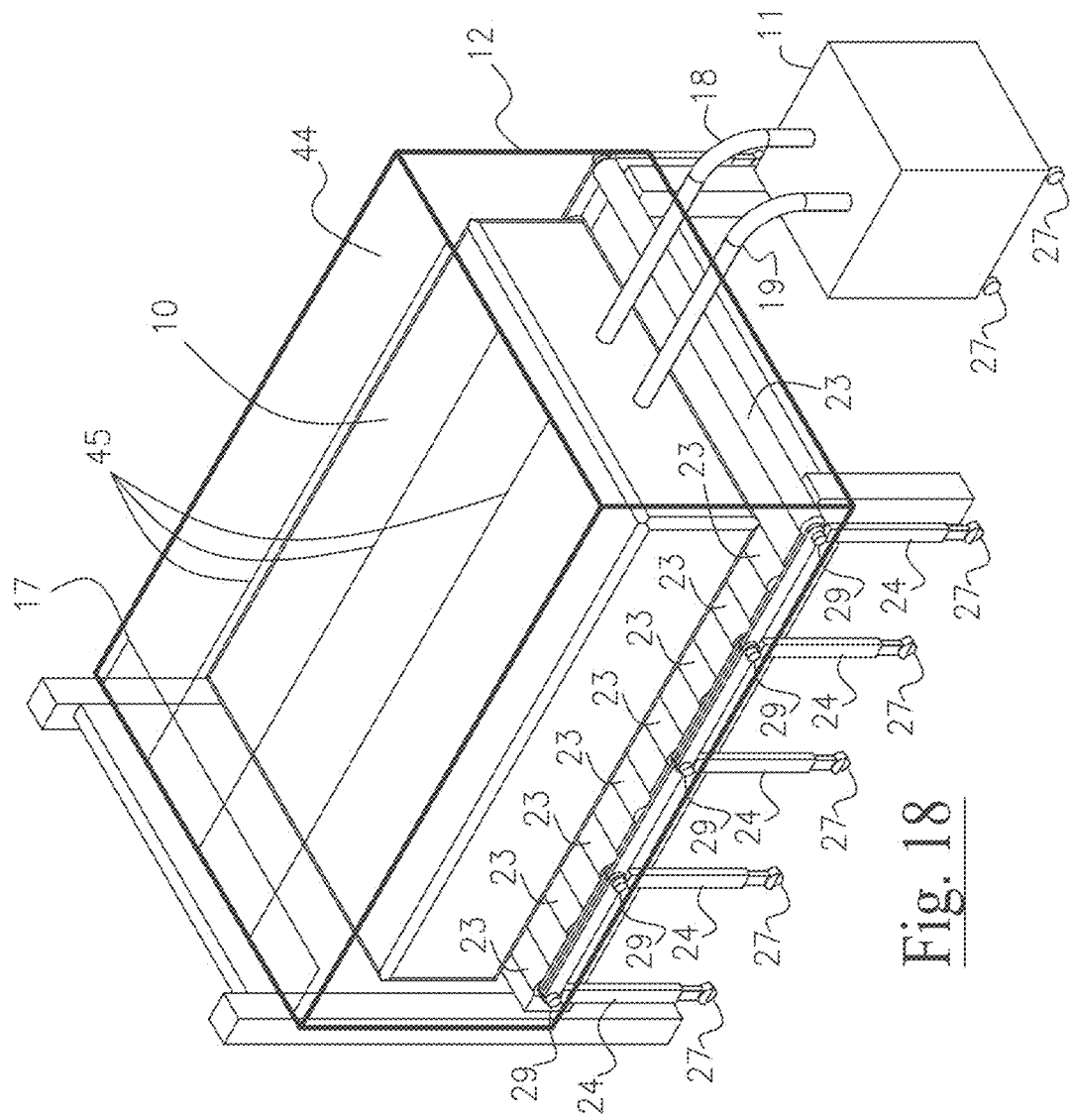
FIG. 18 is a top perspective depiction of a basic bed assembly with a mattress supported by a first alternative barrier delivery mechanism with a gas-impermeable barrier enveloping the mattress and an air treatment apparatus positioned at the first end of the basic bed assembly in circulatory communication with the gas-impermeable barrier for circulating apparatus-treated air therethrough.
Figure 19:
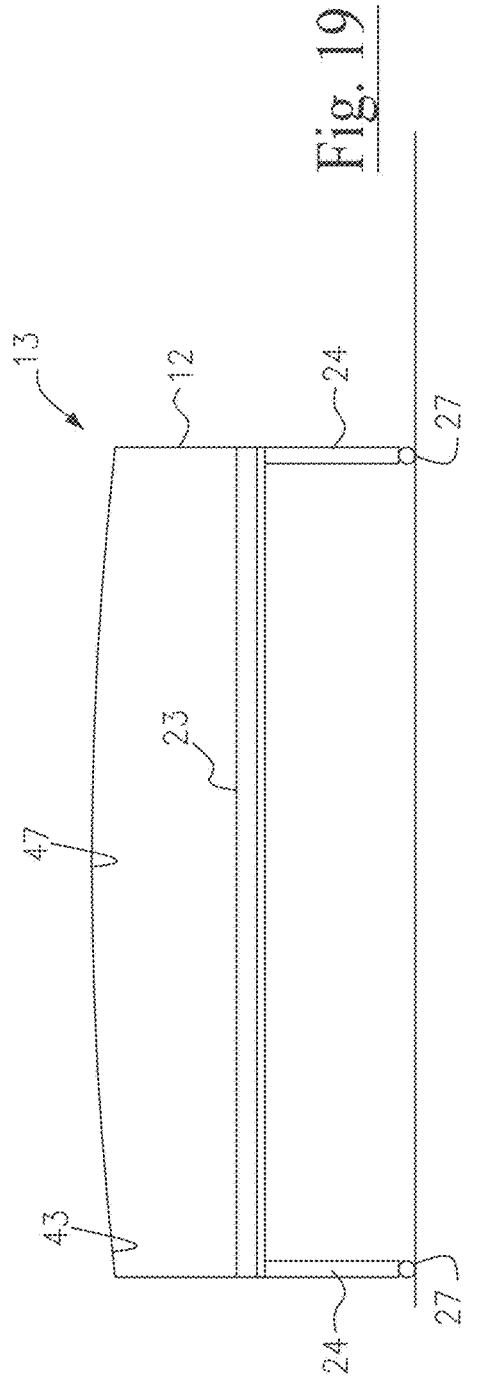
FIG. 19 is a diagrammatic end view depiction of an open barrier mouth end of the first alternative barrier delivery containment apparatus according to the presently disclosed subject matter.
Figure 20:
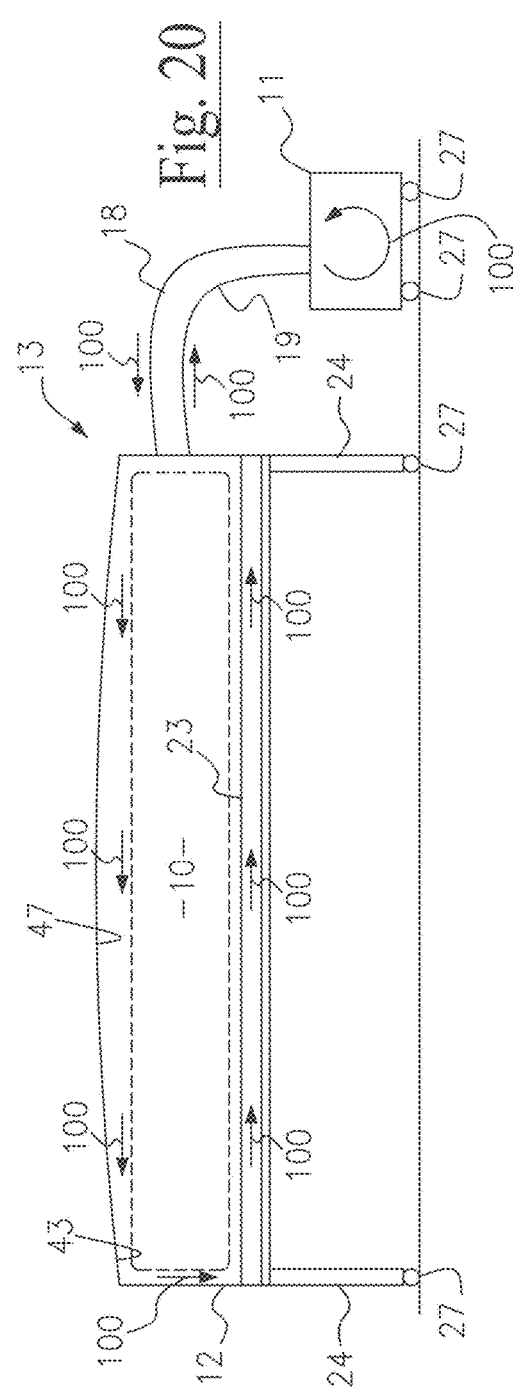
FIG. 20 is a diagrammatic end view depiction of the first alternative barrier delivery containment apparatus shown enveloping a mattress with a portable air treatment apparatus circulating apparatus-treated air through the gas-impermeable barrier for disinfecting the mattress.
Figure 21:
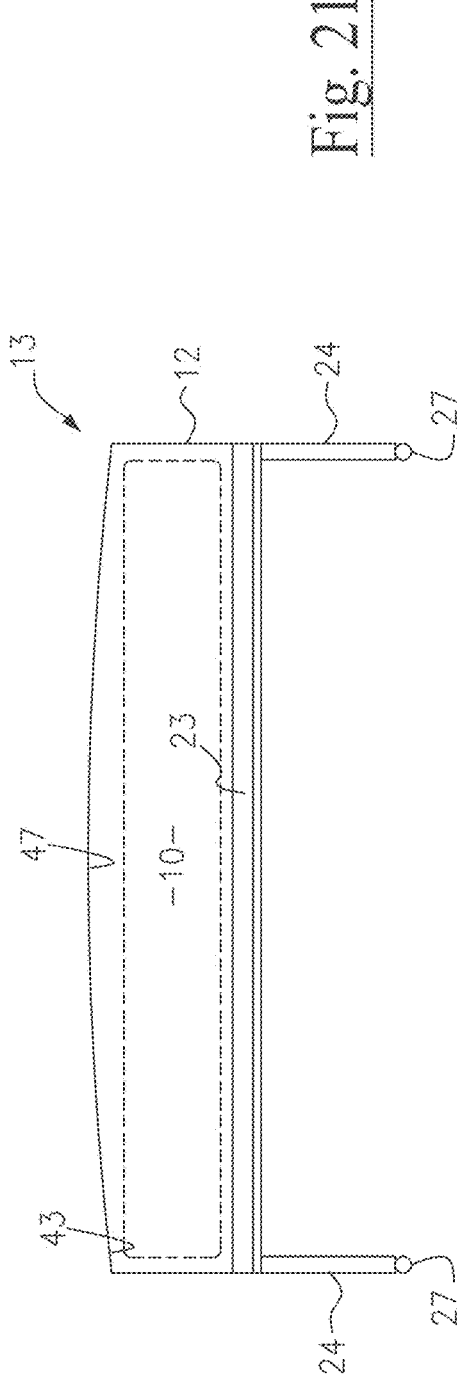
FIG. 21 is a diagrammatic end view depiction of the first alternative barrier delivery containment apparatus according to the presently disclosed subject matter enveloping a mattress.
Figure 22:
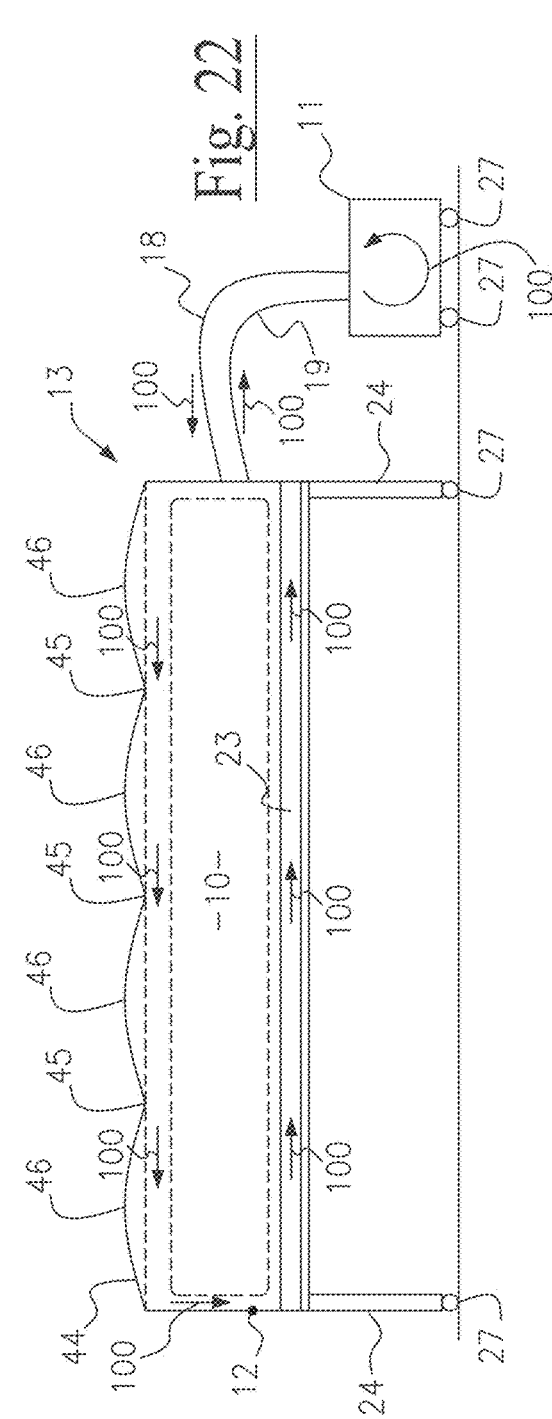
FIG. 22 is a diagrammatic end view depiction of the first alternative barrier delivery containment apparatus shown enveloping a mattress with a portable air treatment apparatus circulating apparatus-treated air through the gas-impermeable barrier with elevated barrier sections to help improve circulation of the apparatus-treated air within the gas-impermeable barrier.

Once the disinfection process is completed (the disinfection/sanitization process preferably takes less than 35 minutes), the gas-impermeable barrier 12 is unzipped by way of the zipper mechanism 17, and the barrier delivery, containment apparatus 13 is pulled back to remove the gas-impermeable barrier 12 and mattress support rollers 23 whereafter the mattress 10 is again supported by its original support structure. As the mattress support rollers 23 are disengaged from the mattress 10, the gas-impermeable barrier 12 is simultaneously removed from the mattress 10. In some embodiments, the barrier delivery, containment apparatus 13 folds accordion style as generally depicted in FIGS. 14 and 17 after disengaging the mattress 10 carrying the gas-impermeable barrier 12 therewith. As the barrier delivery, containment apparatus 13 is removed from the mattress 10, each hinged section 29 may fold with a corresponding barrier section in some embodiments (not specifically illustrated).

The presently disclosed subject matter basically provides an article disinfection system for disinfecting an article exemplified by a mattress as at 10 having an article length 103, an article width 104, and an article height 105. The article disinfection system according to the presently disclosed subject matter essentially comprises, in combination, a barrier delivery, containment apparatus as at 13 or alternatively a barrier delivery, containment apparatus as at 33, and an air treatment apparatus or converter unit as at 11. The barrier delivery, containment apparatus 33 differs from the barrier delivery, containment apparatus 13 by providing a vertically-oriented roller-support frame assembly or carriage 30 instead of a collapsible accordion-style folding apparatus as generally depicted in FIGS. 14 and 17. When not in mattress-disinfecting use, the series of mattress support rollers 23 of the barrier delivery, containment apparatus 33 may be retracted into a vertical orientation and when in mattress-disinfecting use, the series of mattress support rollers 23 may be extended into a horizontal, mattress support orientation or configuration as generally and comparatively depicted in FIGS. 23-26. The vertically-oriented roller-support frame assembly or carriage 30 provides a relatively narrow carriage width as at 106 for enabling an operator to easily install the system unit in tightly spaced rooms and further enables the operator to easily transport the barrier delivery, containment apparatus 33 between rooms for successive multi-mattress/room disinfection/sanitization applications.

Figure 23A:
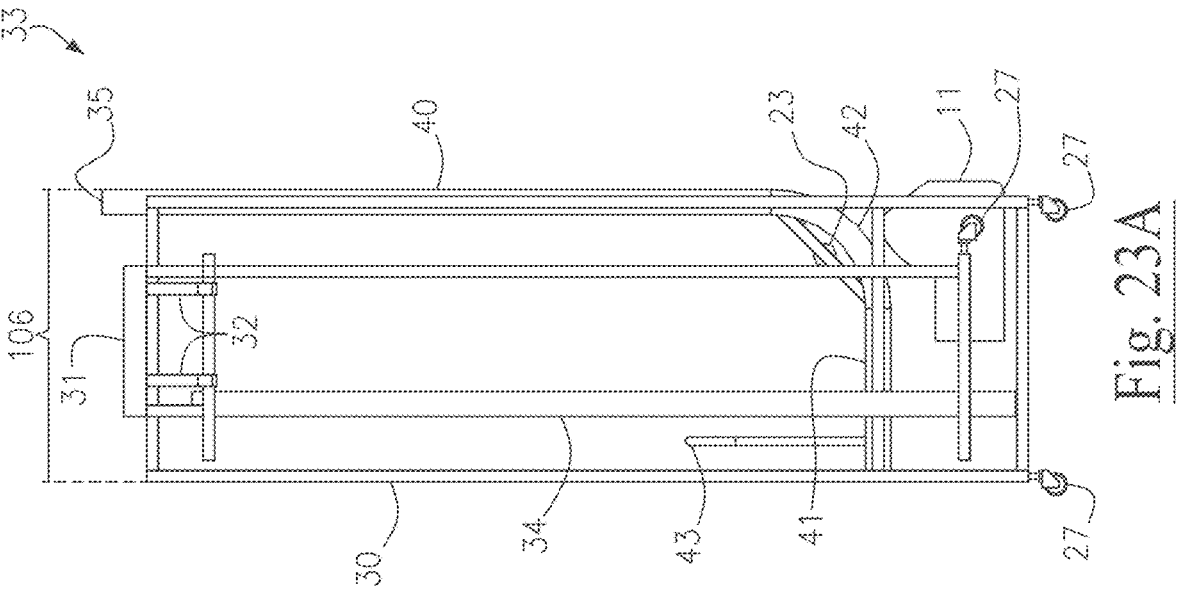
FIG. 23A is side elevational view of the second alternative barrier delivery mechanism according to the presently disclosed subject matter shown in the retracted, stowage configuration.
Figure 23:
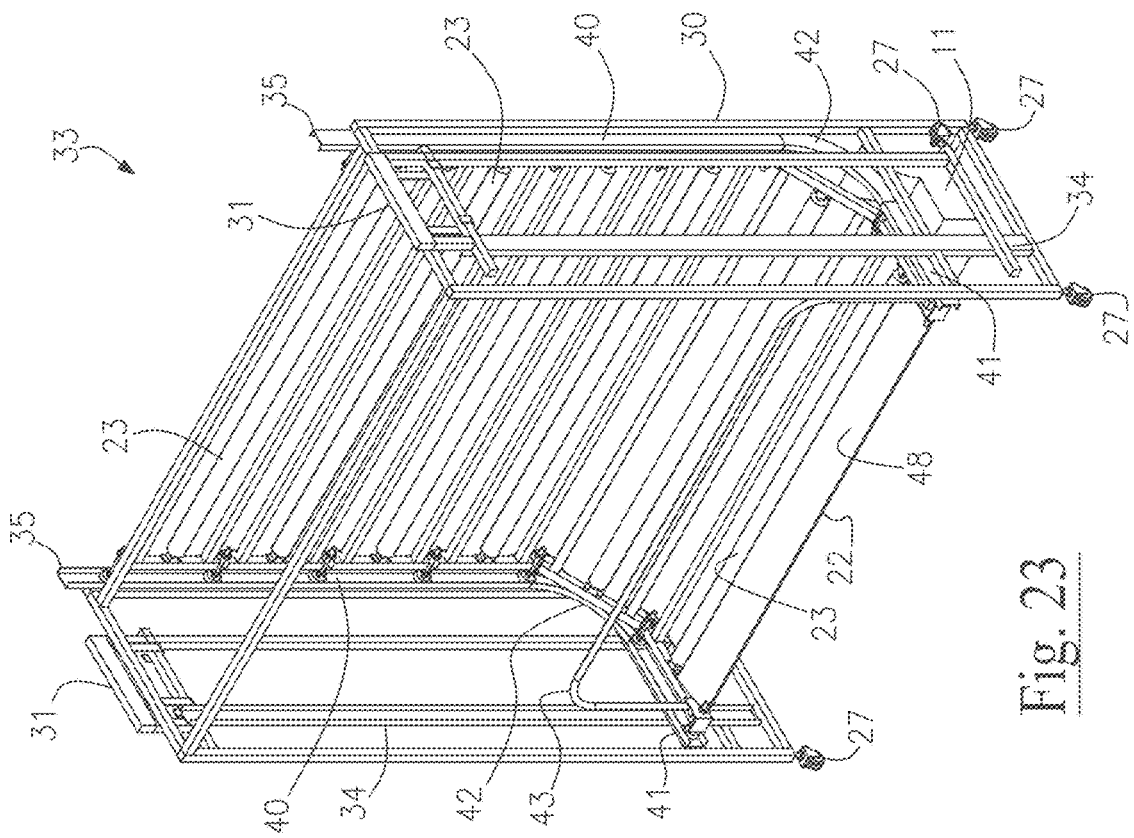
FIG. 23 is an anterior top perspective view of a second alternative barrier delivery mechanism according to the presently disclosed subject matter shown in a retracted, stowage configuration.
Figure 24:
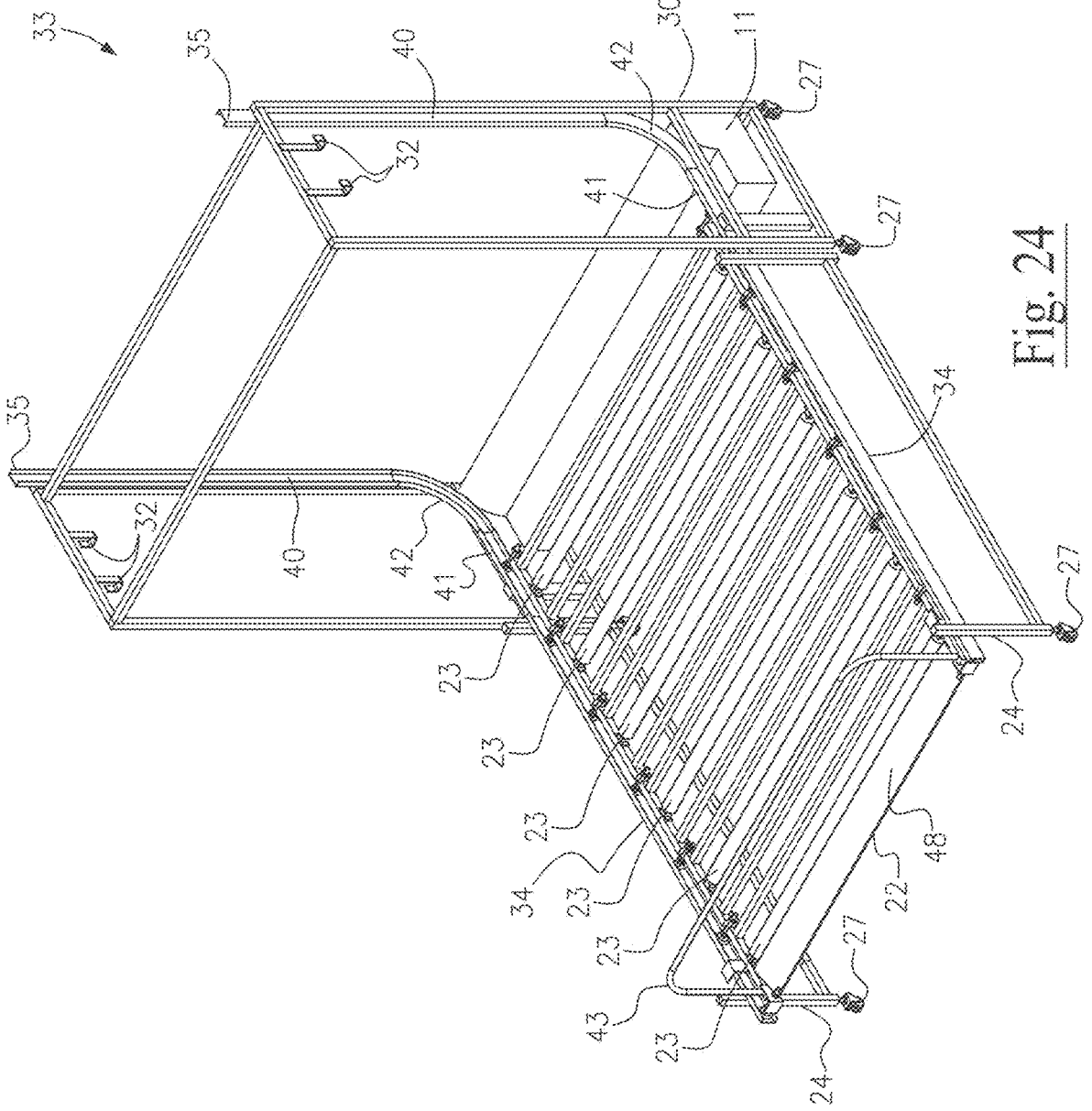
FIG. 24 is an anterior top perspective view of the second alternative barrier delivery mechanism according to the presently disclosed subject matter shown in an extended, mattress-support configuration.
Figure 24A:
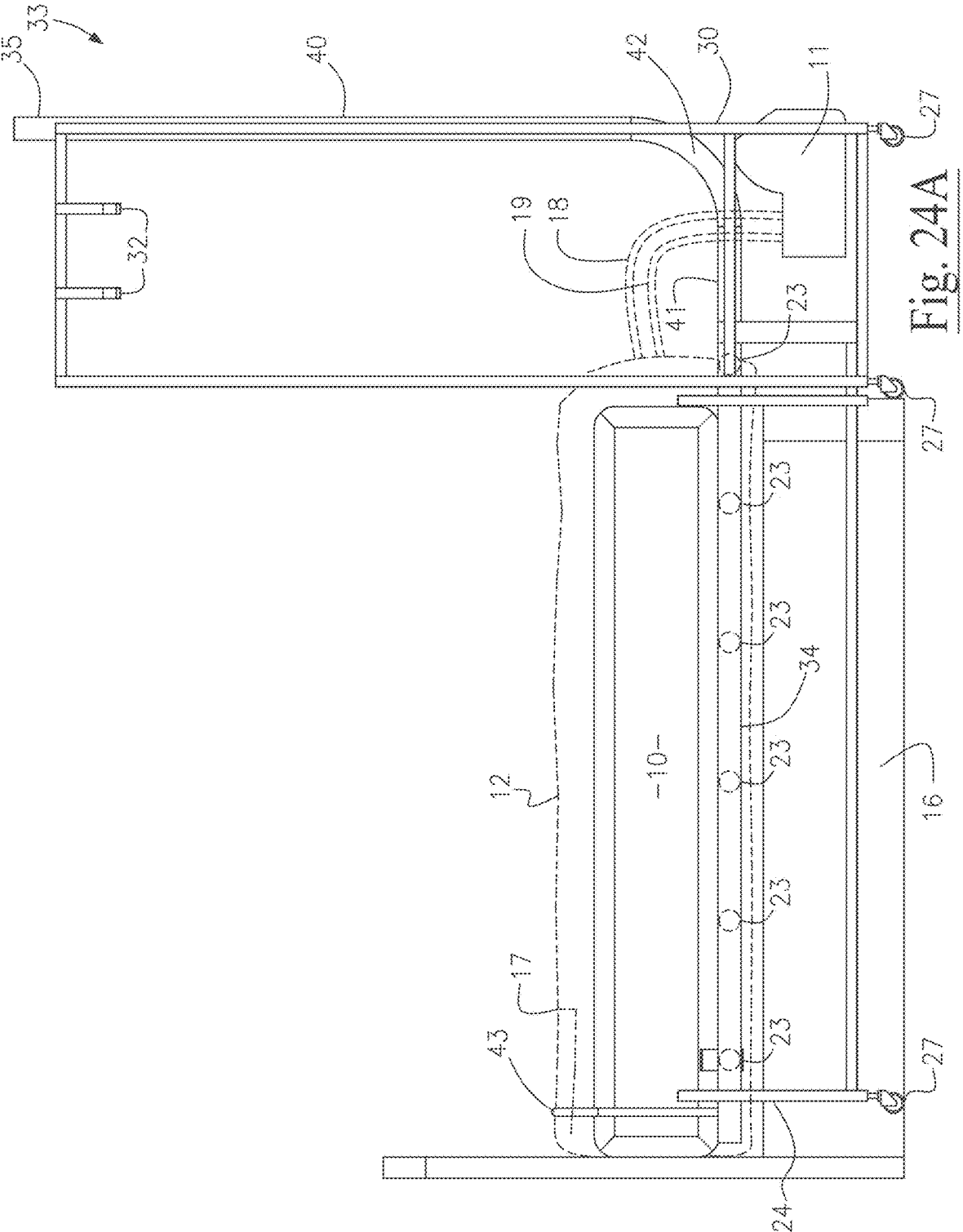
FIG. 24A is side elevational view of the second alternative barrier delivery mechanism according to the presently disclosed subject matter shown in the extended, mattress-support configuration with a gas-impermeable barrier being shown in broken lining in circulatory communication with a carriage-borne air treatment apparatus.
Figure 25:
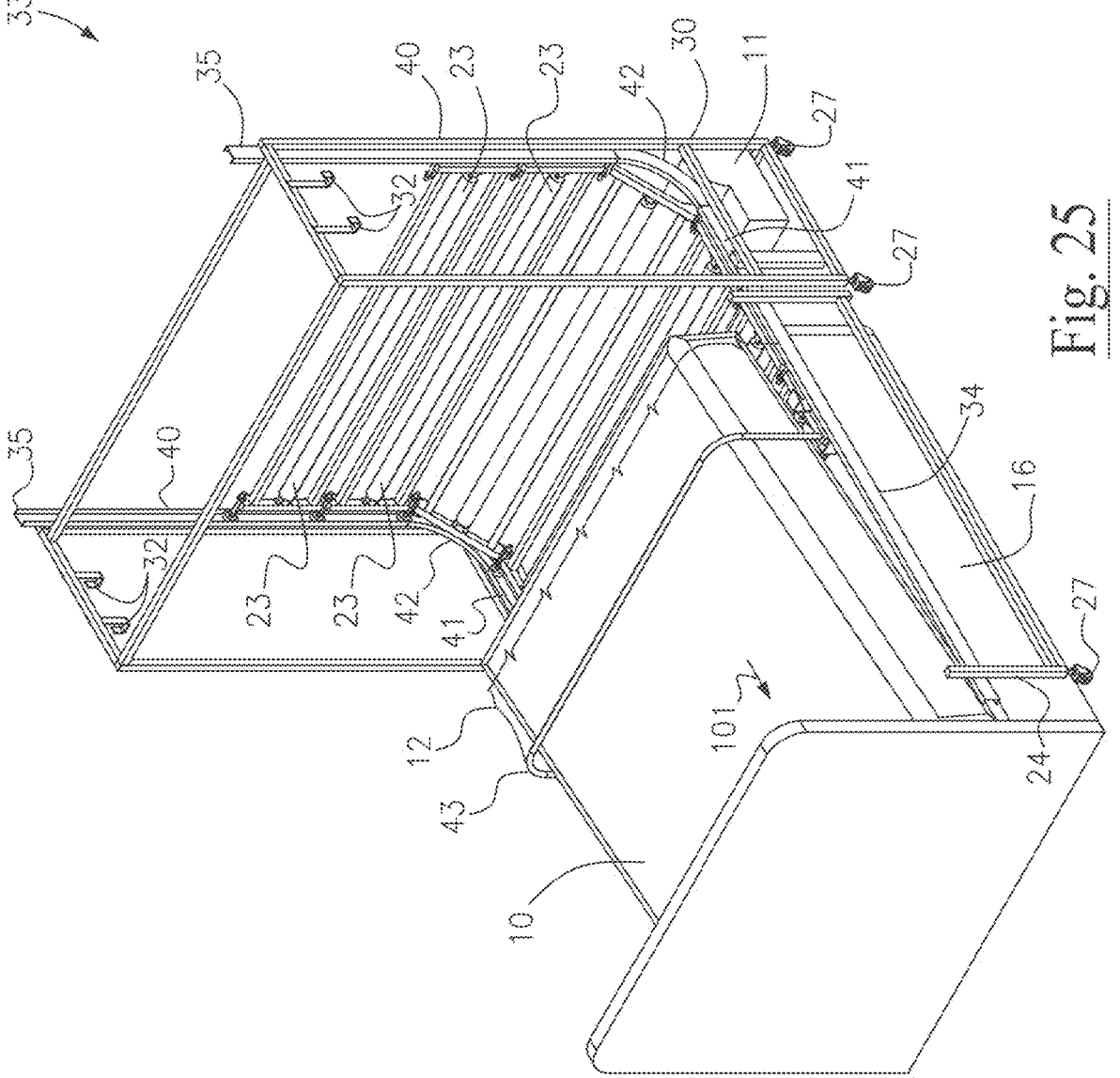
FIG. 25 is an anterior top perspective view of the second alternative barrier delivery mechanism according to the presently disclosed subject matter shown being extended into the mattress-support configuration thereby simultaneously lifting a first end of the mattress and delivering a fragmentary gas-impermeable barrier over the lifted first end of the mattress.
Figure 25A:
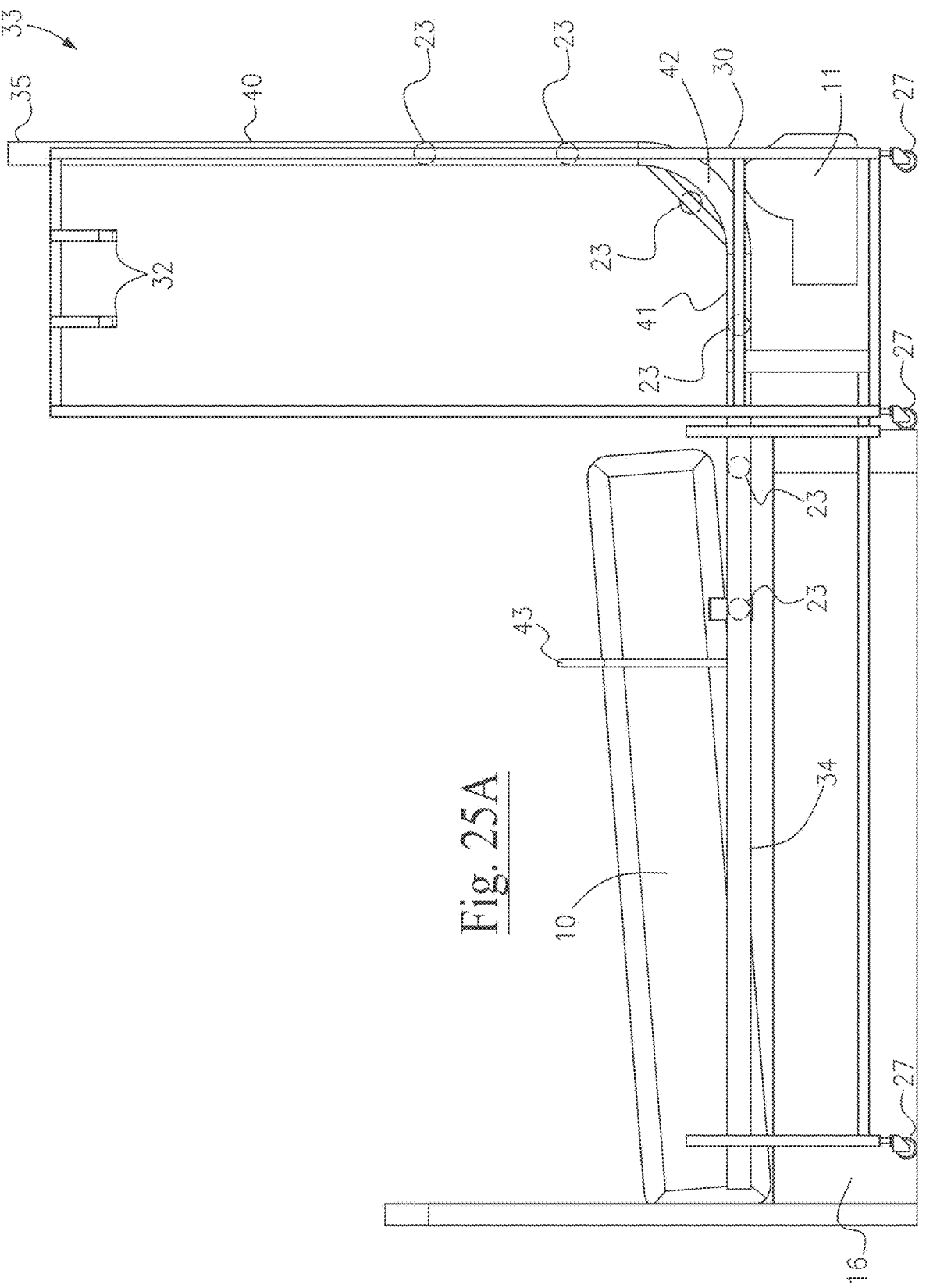
FIG. 25A is side elevational view of the second alternative barrier delivery mechanism according to the presently disclosed subject matter shown being extended into the mattress-support configuration thereby simultaneously lifting the first end of the mattress with the gas-impermeable barrier being removed to show otherwise hidden structures.
Figure 26:
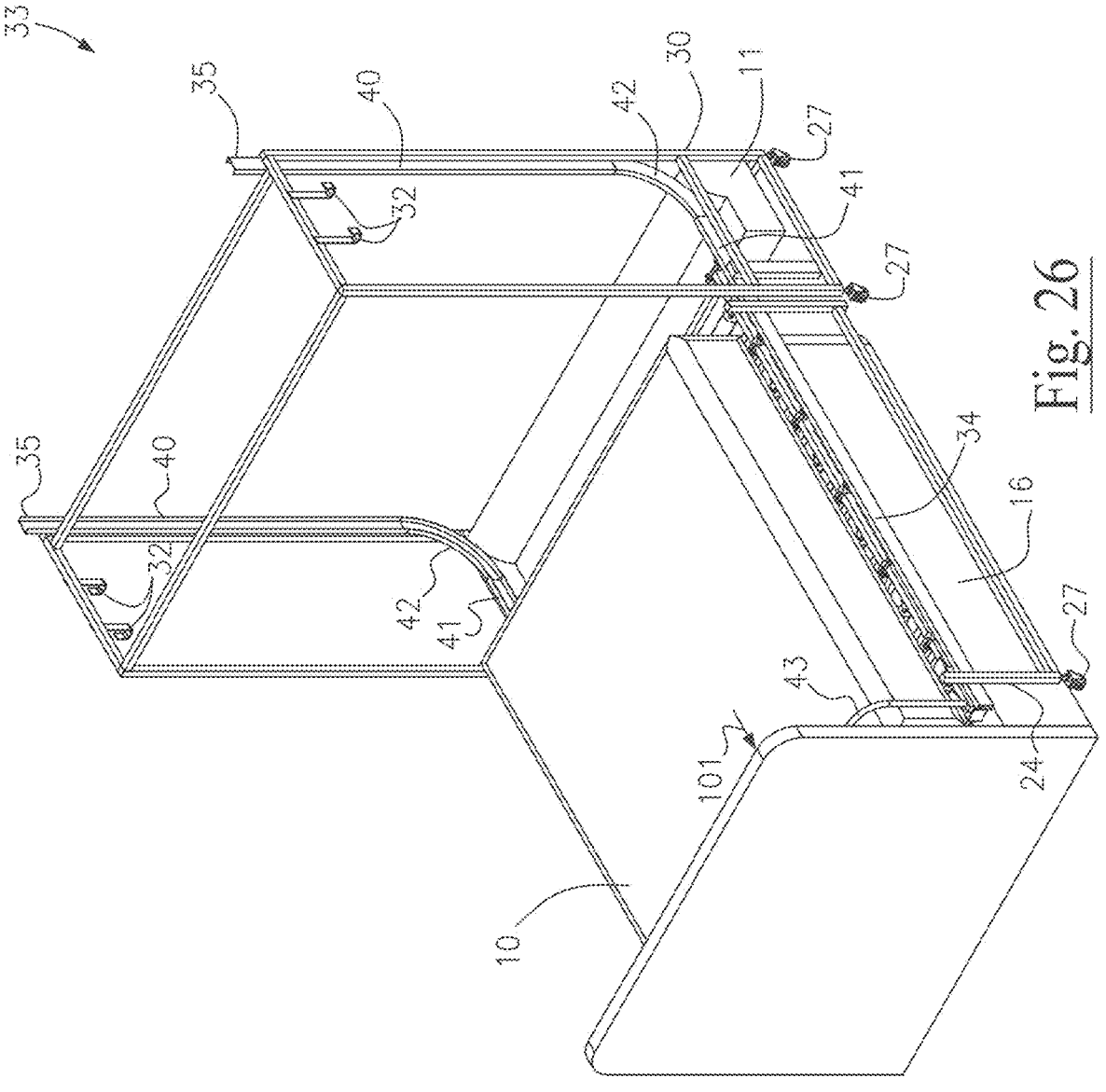
FIG. 26 is an anterior top perspective view of the second alternative barrier delivery mechanism according to the presently disclosed subject matter shown in the fully extended mattress-support configuration with a mattress supported thereby.

When deploying the barrier delivery containment apparatus 33 for mattress-disinfecting use, laterally opposed side rail assemblies 31, otherwise stored upon the vertically-oriented roller-support frame assembly or carriage 30 at laterally opposed pairs of side rail assembly support hooks 32, are deployed in a horizontal orientation as generally and comparatively depicted in FIGS. 23 and 23A versus FIGS. 24 and 24A. The vertically-oriented roller-support frame assembly or carriage 30 comprises laterally opposed side rail assembly support hooks 32 at upper ends of the carriage 30 for holding an upper end of each side rail assembly 31 when not in mattress-disinfecting use thereby vertically storing the side rail assemblies 31 in a compact, portable configuration.

Figure 27:
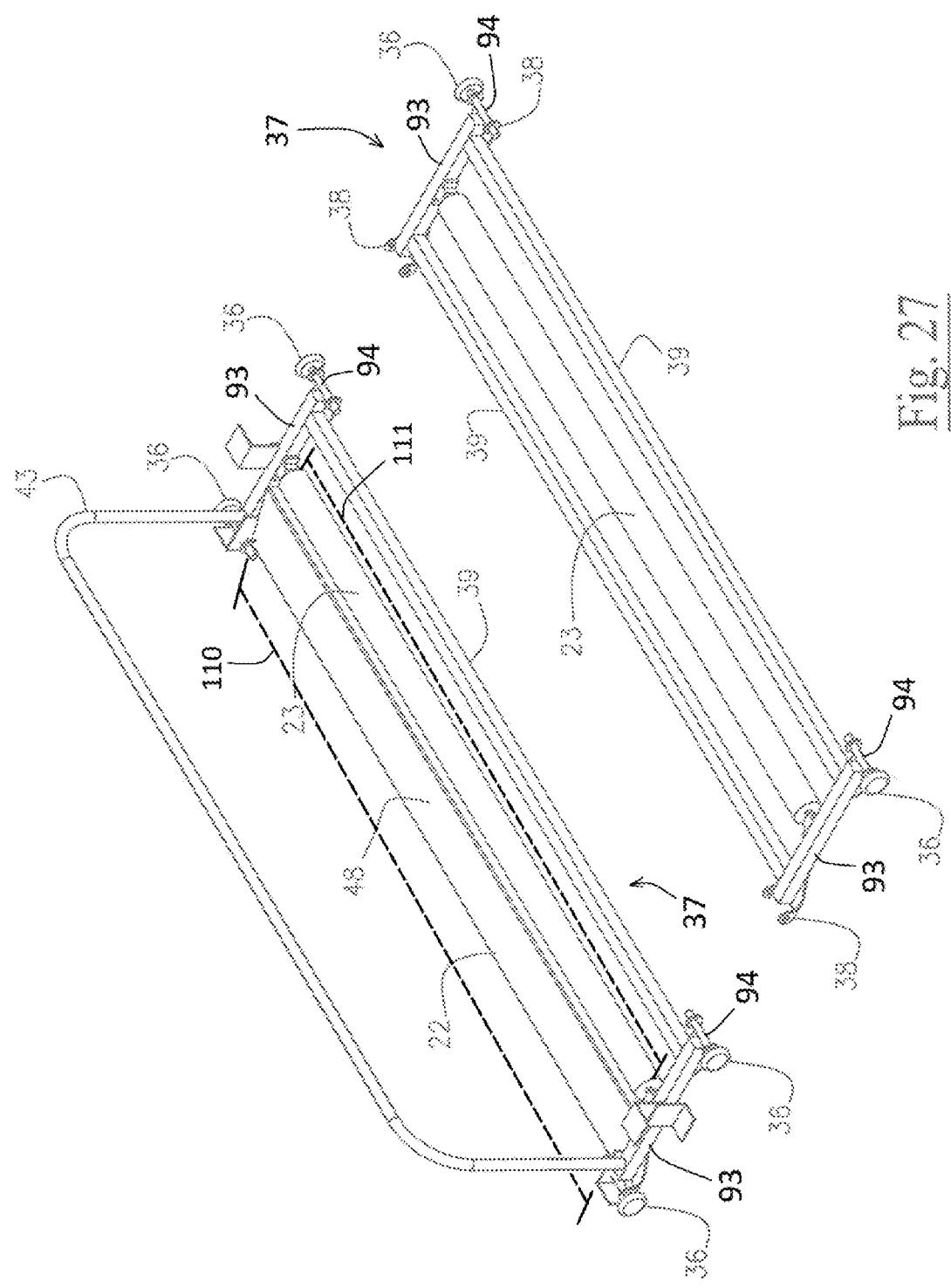
FIG. 27 is a posterior top perspective view of first and second lead frame sections of the second alternative barrier delivery mechanism according to the presently disclosed subject matter including a first lead frame section having a wedge-shaped lead element, a barrier delivery frame, and a mattress support roller and a second frame section having a mattress support roller.
Figure 28:
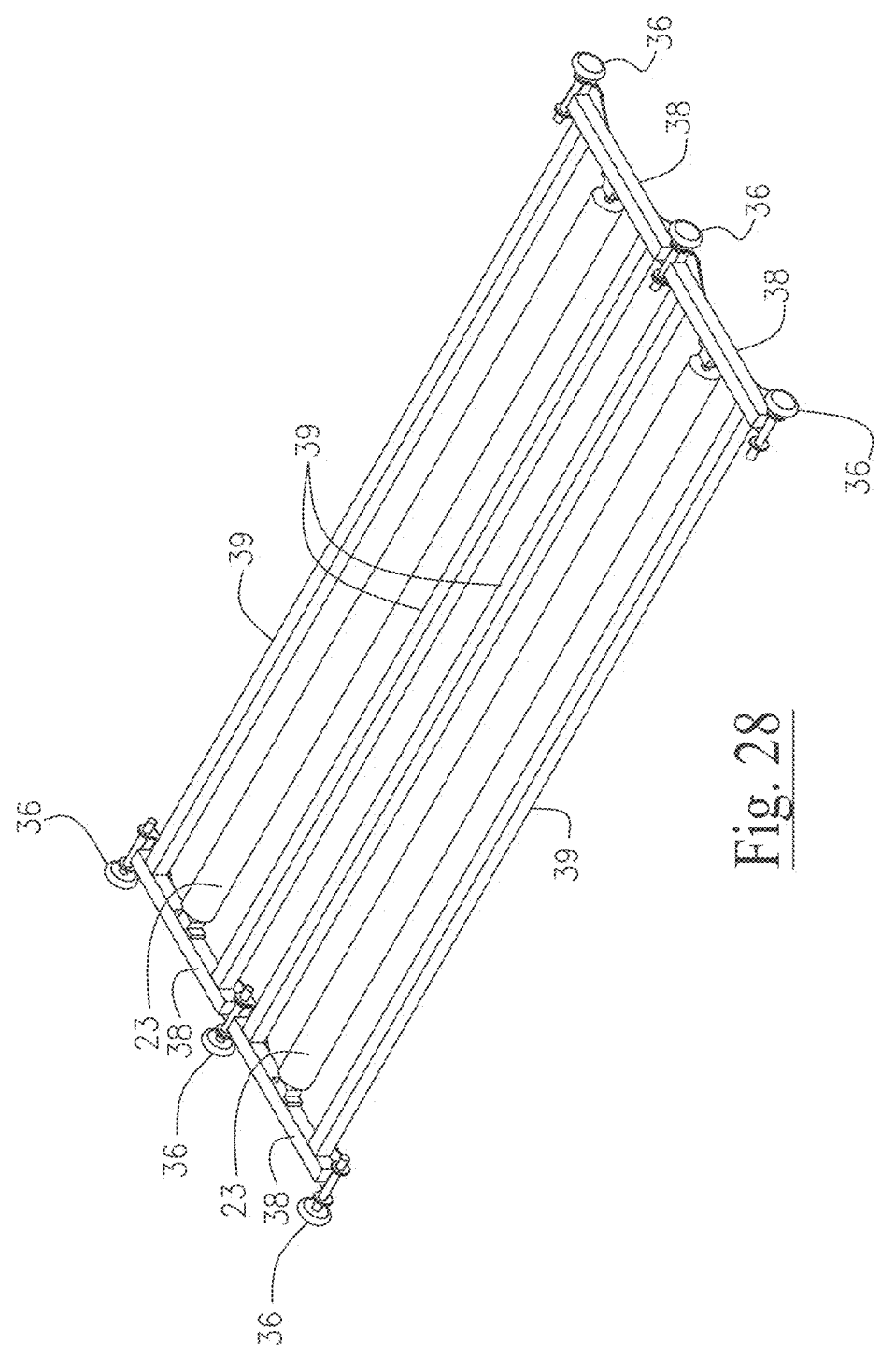
FIG. 28 is an anterior top perspective view of intermediary frame sections of the second alternative barrier delivery mechanism according to the presently disclosed subject matter including a first frame section hingedly connected to a second frame section each of which comprise a centralized mattress support roller.

The side rail assemblies 31 are removed from side rail assembly support hooks 32 attached to upper frame portions of the carriage 30 and attached to the lower end of the vertically-oriented roller-support frame assembly or carriage 30 such that roller-receiving tracks 34 of each side rail assembly 31 are placed in-line with roller-receiving tracks 35 of the vertically-oriented roller-support frame assembly or carriage 30. Roller wheels 36 of conveyor roller segments 37 are rollably received in the roller-receiving tracks 34 and 35. The conveyor roller segments 37 each comprise opposed frame sections 39 supporting a central support roller 23 via frame end portions 93. Adjacent conveyor roller segments 37 are connected by hinge connections 38 interconnected by the roller wheels 36 as generally depicted in FIG. 27. In some embodiments, the roller wheels 36 are located outside the gas-impermeable barrier 12 and attached to the hinged connections 38 of the frame sections 39 of each side rail assembly 31 by way of roller wheel post portions 94 extending through gasketed apertures formed in the gas-impermeable barrier 12 (not specifically illustrated).

Comparatively referencing FIGS. 23-26 it will be seen the roller-receiving tracks 35 each comprise a vertical track portion 40, a horizontal track portion 41, and a radiused track portion 42 intermediate the vertical track portion 40 and the horizontal track portion 41. The horizontal track portion 41 is abbreviated in length relative to the vertical track portion 40 and no longer in length than the carriage width 106 in some embodiments. The side rail assemblies 31 are removed from the side rail assembly support hooks 32 and attached to the lower end of the carriage 30 such that the roller-receiving tracks 34 are aligned with the horizontal track portions 41 thereby providing L-shaped roller-receiving tracks for enabling the series of roller wheels 36 to roll within the tracks 35 and 34 from a vertical stowage configuration to a horizontal mattress containment or application configuration in much the same manner garage doors raise and lower within roller wheel-receiving tracks of a garage door installation. The series of hinged connections 38 of the frame sections 39 of each side rail assembly 31 are configured to pivot at the radiused track portion(s) 42 for enabling the user to either stow the series of mattress support rollers 23 in a vertical configuration or horizontally deploy the series of mattress support rollers 23 between the mattress 10 and its support structure for mattress disinfection/sanitization.

The barrier delivery, containment apparatuses 13 and 33 each comprise at least one gas-impermeable barrier 12 and a barrier delivery mechanism for lifting and supporting an article, exemplified by a mattress 10, within the at least one gas-impermeable barrier 12. The air treatment apparatus or converter unit 11 is attachable to the at least one gas-impermeable barrier 12 and configured to circulate apparatus-treated air therethrough for immersing the article or mattress 10 in circulating heated or ozonated apparatus-treated air for article disinfection. The gas-impermeable barrier 12 comprises a barrier length 107, a barrier width 108, and a barrier height 109. The barrier length 107, the barrier width 108, and the barrier height 109 are respectively greater than the article length 103, article width 104, and article height 105 so as to fully envelope or encase the mattress 10. The barrier delivery, containment apparatuses 13 and 33 are configured to maximize an internal volume of the gas-impermeable barrier 12 in some embodiments for enhancing circulation of the apparatus-treated air therewithin.

As noted hereinabove, the article or mattress 10 may be supported by a support structure as exemplified by either a bed frame 16 or a box spring as at 15. The barrier delivery, containment apparatuses 13 and 33 each comprise a front end as at 25, a rear end as at 26, and a series of article or mattress support rollers 23 intermediate the front end 25 and the rear end 26. A lower portion of the front end 25 is preferably outfitted with a wedge-shaped lead element 22 in some embodiments. The wedge-shaped lead element 22 is insertable intermediate the article or mattress 10 and the support structure for elevating the article or mattress 10 relative to the support structure. The series of mattress support rollers 23 enable the article or mattress 10 to roll thereatop. The front end 25 comprises a barrier mouth frame 43 that attaches to the open front end of the gas-impermeable barrier 12 for holding open the open front end of the gas-impermeable barrier 12. In some embodiments, the gas-impermeable barrier 12 envelopes the series of mattress support rollers 23 and the article or mattress 10 while apparatus-treated air circulates as at 100 within the gas-impermeable barrier 12.

In some embodiments, the gas-impermeable barrier 12 may comprise a top surface 44 with a series of striated seal sections as at 45. The series of striated seal sections 45 extend intermediate the front end 25 and the rear end 26 and are arranged in parallel relation lengthwise relative to the gas-impermeable barrier 12 for providing a series of elevated barrier sections 46 when apparatus-treated air is circulated in and around the article or mattress 10. The elevated barrier sections 46 help improve circulation of the apparatus-treated air within the gas-impermeable barrier 12 in these embodiments. As noted, in some embodiments, the barrier delivery, containment apparatuses 13 and 33 comprise a barrier mouth frame 43 at the front end 25. The barrier mouth frame 43 may comprise an arcuate upper frame portion 47 in some embodiments. The arcuate upper frame portion 47 elevates a front mouth portion of the gas-impermeable barrier 12 as the barrier delivery, containment apparatuses 13 and 33 envelope or encase the article or mattress 10.

As noted above, the barrier delivery, containment apparatuses 13 and 33 may preferably comprise an angled or wedge-shaped lead element as at 22. The angled or wedge-shaped lead element 22 wedges intermediate the article or mattress 10 and its support structure as the barrier delivery, containment apparatuses 13 and 33 envelope the article or mattress 10 with the gas-impermeable barrier 12. The angled or wedge-shaped lead element 22 is essentially a triangular shaped tool for providing an inclined plane to separate two objects or portions of an object or lift up an object relative to a support object. It functions by converting a vectored force as at 101 applied to its blunt end into forces perpendicular or normal to its inclined surface 48 of the wedge-shaped lead element 22.

Figure 29:
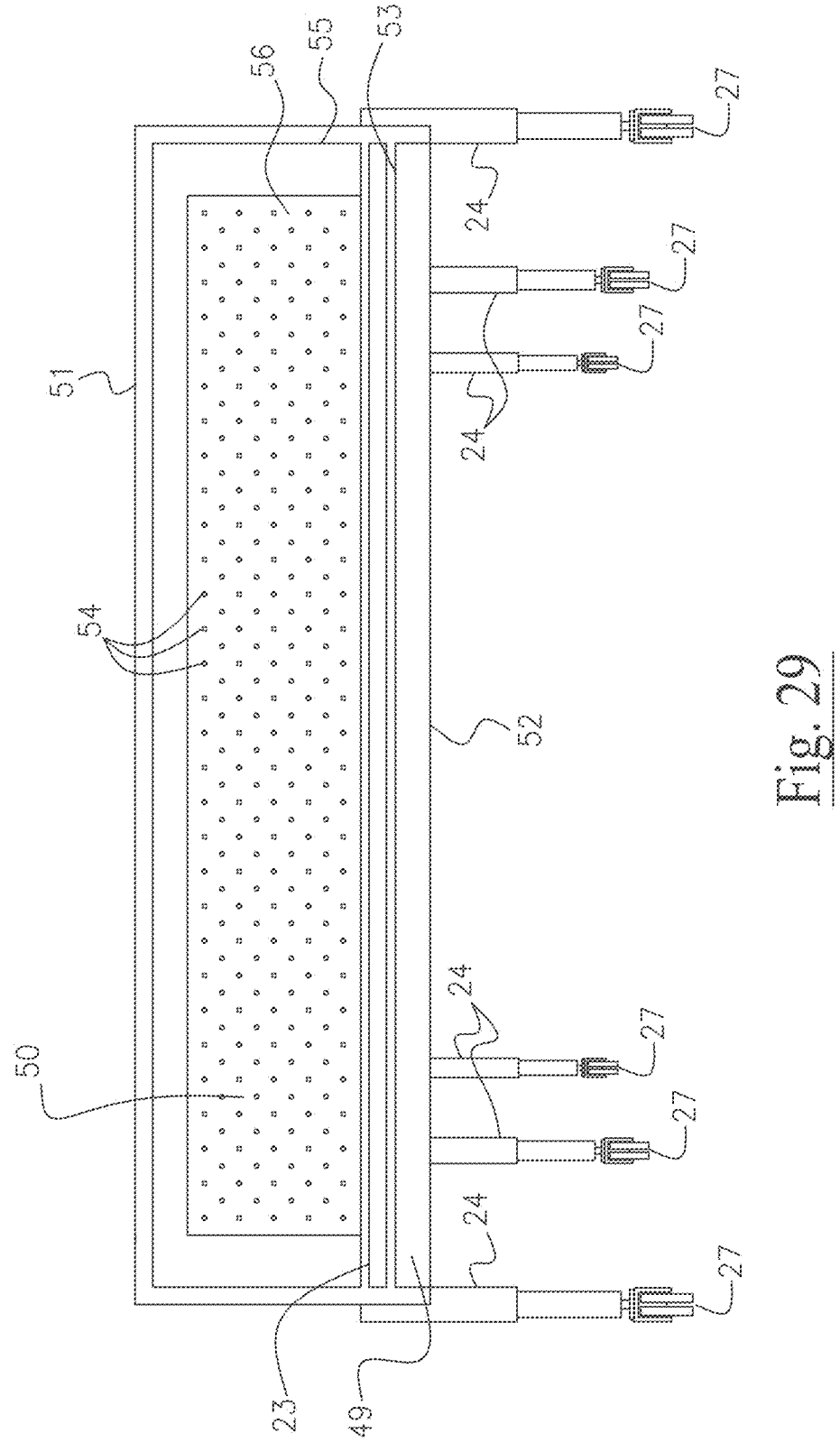
FIG. 29 is a diagrammatic perspective end view depiction of an alternative layered gas-impermeable barrier arrangement according to the presently disclosed subject matter, the layered gas-impermeable barrier arrangement comprising an interior bottom bladder barrier, an interior top bladder barrier, and an exterior over-barrier.
Figure 30:
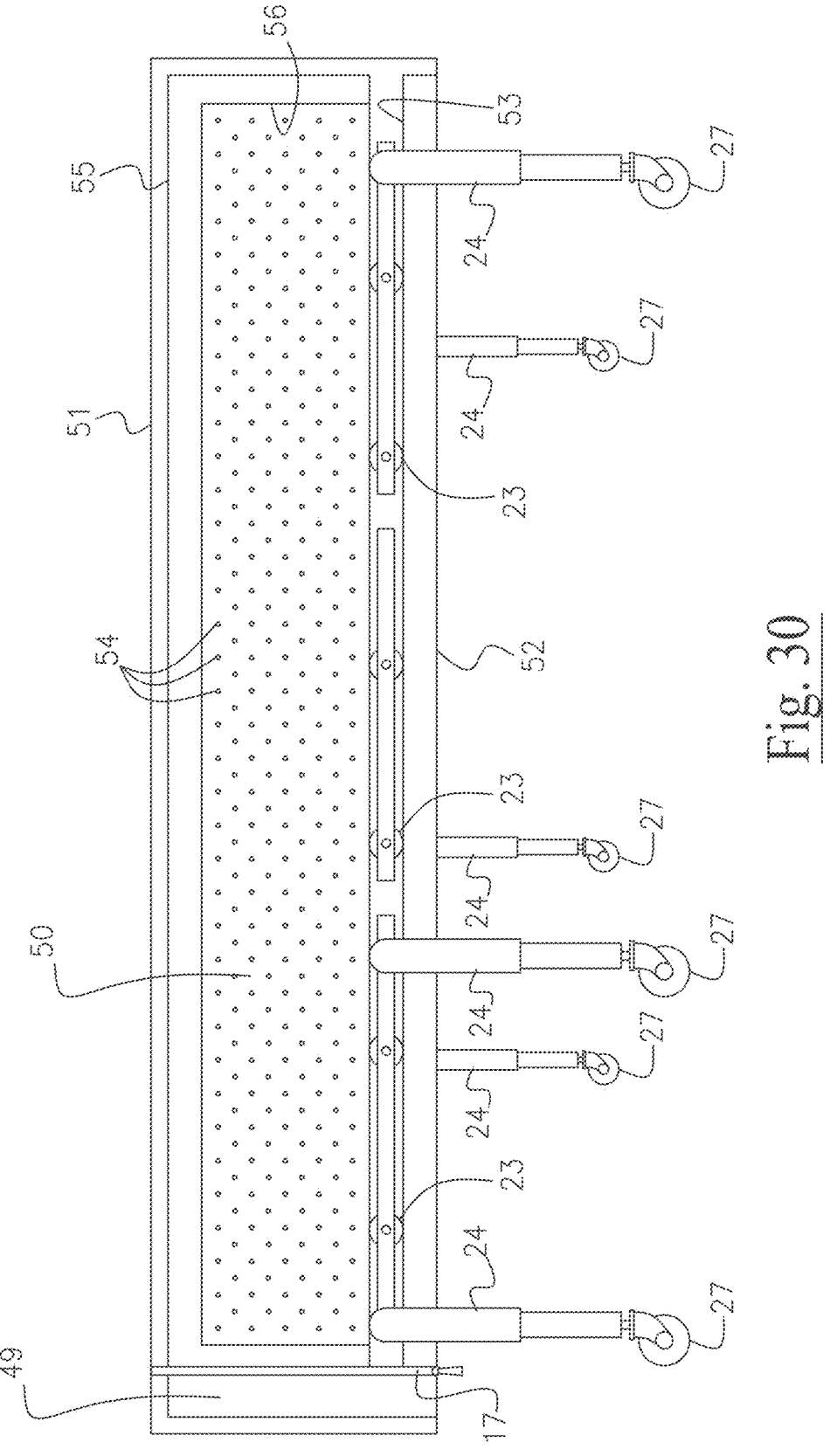
FIG. 30 is a diagrammatic perspective side view depiction of the alternative layered gas-impermeable barrier arrangement according to the presently disclosed subject matter.
Figure 31:
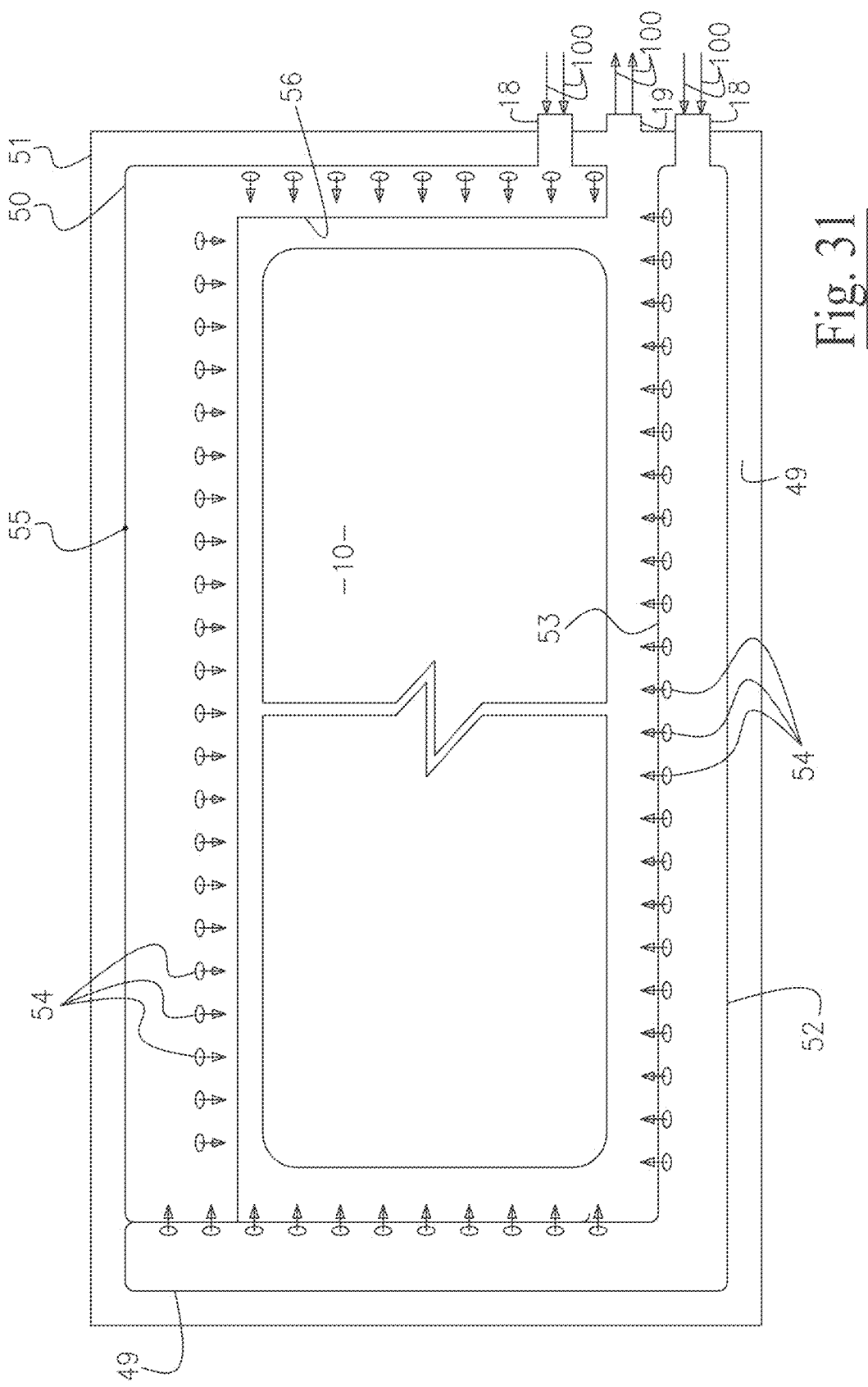
FIG. 31 is a diagrammatic depiction of the circulatory path of apparatus-treated air through the alternative layered gas-impermeable barrier arrangement according to the presently disclosed subject matter.

In certain embodiments, the barrier delivery, containment apparatuses 13 and 33 according to the presently disclosed subject matter may comprise a series of layered gas-impermeable barriers or a layered gas-impermeable barrier arrangement as generally and comparatively depicted in FIGS. 29-31. The series of layered gas-impermeable bladders include an interior bottom bladder barrier 49, an interior top bladder barrier 50, and an exterior over-barrier 51. The interior bottom bladder barrier 49 and the interior top bladder barrier 50 are used to distribute the apparatus-treated air around all sides of the article or mattress 10. The exterior over-barrier 51 encases the interior bottom bladder barrier 49 and the interior top bladder barrier 50 enveloping the article or mattress 10 and the interior bottom/top bladder barriers 49 and 50 in an airtight seal to keep the heated or ozonated apparatus-treated air in and around the mattress 10 and the internal bottom and top bladder barriers 49/50. The exterior over-barrier 51 also collects the apparatus-treated air after it is applied to the article or mattress 10 to be sent back to the ozone generator or converter unit 11 for supplemental ozone (to maintain the ozone levels at a therapeutic concentration (2 ppm to 4 ppm) or for supplemental heat to maintain the proper temperature depending on the cycle the system is running.

The interior bottom bladder barrier 49 comprises a top barrier surface 53 and a bottom barrier surface 52. The top barrier surface 53 faces or opposes lower mattress surfacing of the mattress 10 and directs heated or ozonated apparatus-treated air toward the lower mattress surfacing. The heated or ozonated apparatus-treated air is introduced into the interior bottom bladder barrier 49 via a first inlet line/hose 18 which heated or ozonated apparatus-treated air permeates the volumetric space within the interior bottom bladder barrier 49 and exits the same through a series of apertures 54 formed in the top barrier surface 53. The interior top bladder barrier 50 comprises a top barrier surface 55 and a bottom barrier surface 56. The bottom barrier surface 56 faces or opposes upper mattress surfacing of the mattress 10 and directs heated or ozonated apparatus-treated air toward the upper mattress surfacing. The heated or ozonated apparatus-treated air is introduced into the interior top bladder barrier 50 via a second inlet line/hose 18 which heated or ozonated apparatus-treated air permeates the volumetric space within the interior top bladder barrier 50 and exits the same through a series of apertures 54 formed in the bottom barrier surface 56. The exterior over-barrier 51 collects the apparatus-treated air after it is applied to the mattress 10 to be sent back to the ozone generator or converter unit 11 via an outlet line/hose 19 to exhaust materials to the converter unit 11 or for supplemental ozone or for supplemental heat.

While the above descriptions contain much specificity, this specificity should not be construed as limitations on the scope of the invention, but rather as an exemplification of the invention. In certain embodiments, the basic invention may be said to essentially teach or disclose a disinfection system and method for disinfecting an article or mattress having an article length, an article width, and an article height. The disinfection system according to the presently disclosed subject matter essentially comprises, in combination a barrier delivery, containment apparatus and an air treatment apparatus. The barrier delivery, containment apparatus comprises at least one gas-impermeable barrier and a barrier delivery mechanism for lifting and supporting the article or mattress within the at least one gas-impermeable barrier. The air treatment apparatus is attachable to the at least one gas-impermeable barrier and configured to circulate apparatus-treated air through the at least one gas-impermeable barrier for disinfecting the article or mattress as lifted and supported therewithin.

In some embodiments, the gas-impermeable barrier comprises a barrier length, a barrier width, and a barrier height. The barrier length, the barrier width, and the barrier height are respectively greater than the article length, article width, and article height so as to fully envelope the article. The barrier delivery mechanism (i.e. the structures of the barrier delivery, containment apparatus that support delivery of the gas-impermeable barrier) is configured to maximize an internal volume of the at least one gas-impermeable barrier for enhancing circulation of the apparatus-treated air therewithin.

In some embodiments, the article or mattress is supported by a support structure. The barrier delivery mechanism comprises a front end, a rear end, and a series of article or mattress support rollers intermediate the front and rear ends. The front end is insertable intermediate the article or mattress and the article or mattress support structure for elevating the article or mattress relative to the article or mattress support structure. The series of article or mattress support rollers enable the article or mattress to roll thereatop. The at least one gas-impermeable barrier envelopes the series of article or mattress support rollers and the article or mattress while the apparatus-treated air circulates within the at least one gas-impermeable barrier.

In some embodiments, the barrier delivery, containment apparatus is height adjustable to accommodate differences in height of the article or mattress support structure relative to the support surface or floor. In some embodiments, the barrier delivery mechanism comprises a wedge-shaped lead element, which wedge-shaped lead element wedges intermediate the article or mattress and the article or mattress support structure as the barrier delivery mechanism envelopes the article or mattress within the gas-impermeable barrier. In some embodiments, the barrier delivery, containment apparatus is collapsible and portable, either by way of an accordion style collapse mechanism as illustrated in connection with barrier delivery, containment apparatus 12 or a roller-retraction mechanism as illustrated in connection with barrier delivery, containment apparatus 33. both of which apparatuses 13 and 33 are preferably outfitted with castors 37 or similar other roller means for portable movement.

It will thus be seen that in some embodiments, the barrier delivery, containment apparatus comprises a vertical stowage configuration and a horizontal application configuration. In these embodiments, the barrier delivery mechanism is retractable into the vertical stowage configuration for easing or enhancing portability of the disinfection system. In these embodiments, the front end of the barrier delivery mechanism is configured for ready insertion intermediate the article or mattress and the article or mattress support structure when the barrier delivery mechanism is retracted into the vertical stowage configuration.

In some embodiments, the barrier delivery, containment apparatus comprises a series of gas-impermeable barriers or a layered gas-impermeable barrier arrangement including an interior bottom bladder barrier, an interior top bladder barrier, and an exterior over-barrier. The interior bottom bladder barrier and the interior top bladder barrier direct apparatus-treated air against article or mattress surfacing. The exterior over-barrier envelopes or encases the interior bottom bladder barrier and the interior top bladder barrier and exhausts apparatus-treated air back to the air treatment apparatus, disinfection generator or converter unit. The interior bottom bladder barrier and the interior top bladder barrier each preferably further comprise article-opposing surfacing comprising a series of grid-patterned apertures. The series apertures help direct apparatus-treated air against the article or mattress surfacing.

What is claimed is:

1. A disinfection method for disinfecting an article, the disinfection method comprising the steps of:

supporting an article vertically by a support structure, the article having an article width and an article length, the article and support structure being horizontally stationary;

positioning a barrier delivery, containment apparatus at a first end of the article, the barrier delivery, containment apparatus comprising at least one gas-impermeable barrier and a barrier delivery mechanism;

the barrier delivery mechanism comprising a front end, a rear end, and a plurality of support rollers extending in spaced relation to one another intermediate the front and rear ends, the plurality of support rollers each having a roller length at least equal to the article width;

the front end comprising a wedge-shaped lead element extending in parallel relation to a first support roller at the front end, the wedge-shaped lead element having an element length at least equal to the roller length;

directing the barrier delivery mechanism toward the article such that the wedge-shaped lead element wedges intermediate the article and the support structure remaining horizontally stationary thereby raising the article and enabling the article to roll atop the plurality of support rollers as the barrier delivery mechanism is directed along the article length;

simultaneously enveloping the article within the at least one gas-impermeable barrier while the barrier delivery mechanism is directed along the article length; and circulating apparatus-treated air through the at least one gas-impermeable barrier by way of an air treatment apparatus in circulatory communication therewith.

2. The disinfection method according to claim 1, wherein the barrier delivery mechanism comprises opposed roller-receiving tracks;

the plurality of support rollers being supported by frame sections of conveyor roller segments rollably received in the opposed roller-receiving tracks by roller wheels;

the roller wheels being located outside the gas-impermeable barrier and attached to the frame sections by way of gasketed apertures formed in the gas-impermeable barrier, the gas-impermeable barrier enveloping the support rollers and the article while apparatus-treated air circulates within the gas-impermeable barrier.

3. The disinfection method according to claim 1 comprising the step of adjusting a height of the front end and the rear end such that the wedge-shaped lead element is height positioned intermediate the article and the support structure before the barrier delivery mechanism is directed theretoward.

4. The disinfection method according to claim 1, wherein the barrier delivery, containment apparatus is reconfigurable intermediate a stowage configuration and an application configuration, the barrier delivery mechanism of the barrier delivery containment apparatus being directed into the application configuration from the stowage configuration while directing the barrier delivery mechanism along the article length.

5. The disinfection method according to claim 4, wherein the barrier delivery, containment apparatus comprises a vertical stowage configuration and a horizontal application configuration, the barrier delivery mechanism being retractable into the vertical stowage configuration for portability of the barrier delivery, containment apparatus after circulating apparatus-treated air through the at least one gas-impermeable barrier.

6. The disinfection method according to claim 5, wherein the wedge-shaped lead element is height adjusted for horizontal insertion intermediate the article and the support structure before the barrier delivery mechanism is directed into the horizontal application configuration.

7. The disinfection method according to claim 1, wherein the barrier delivery, containment apparatus comprises a plurality series of layered gas-impermeable barriers including an interior bottom bladder barrier, an interior top bladder barrier, and an exterior over-barrier, the interior bottom bladder barrier and the interior top bladder barrier for directing apparatus-treated air against article surfacing, the exterior over-barrier for enveloping the interior bottom bladder barrier and the interior top bladder barrier and exhausting apparatus-treated air back to the air treatment apparatus.

8. The disinfection method according to claim 7, wherein the interior bottom bladder barrier and the interior top bladder barrier each comprise article-opposing surfacing, the article-opposing surfacing comprising a plurality of apertures, the plurality of apertures for directing apparatus-treated air against article surfacing.

9. The disinfection method according to claim 1, wherein the air treatment apparatus treats air by at least one of ozonating the air and heating the air.

10. A disinfection method for disinfecting an article, the disinfection method comprising the steps of:

providing a barrier delivery, containment apparatus, the barrier delivery, containment apparatus comprising opposed roller-receiving tracks, a gas-impermeable barrier and a barrier delivery mechanism;

the gas-impermeable barrier being configured to encase the article via a closable open end;

the barrier delivery mechanism comprising a front end, a rear end, and a plurality of support rollers extending in spaced relation to one another intermediate the front and rear ends;

the plurality of support rollers being supported by frame sections of conveyor roller segments rollably received in the opposed roller-receiving tracks by roller wheels;

the roller wheels being located outside the gas-impermeable barrier and attached to the frame sections by way of gasketed apertures formed in the gas-impermeable barrier;

positioning the closable open end adjacent a first side of the article;

directing the barrier delivery mechanism along an article length of the article thereby simultaneously lifting and supporting the article while enveloping the article within the gas-impermeable barrier;

closing the closable open end at a second side of the article opposite the first side thereby encasing the article within the gas-impermeable barrier; and circulating apparatus-treated air through the gas-impermeable barrier in adjacency to the article as encased within the gas-impermeable barrier thereby immersing the article in the circulating apparatus-treated air;

the gas-impermeable barrier enveloping both the support rollers and the article while apparatus-treated air circulates within the gas-impermeable barrier.

11. The disinfection method according to claim 10, wherein the article is supported by a support structure, the article having an article width;

the plurality of support rollers each having a roller length at least equal to the article width;

the front end comprising a wedge-shaped lead element extending in parallel relation to a first support roller at the front end, the wedge-shaped lead element having an element length at least equal to the roller length;

directing the barrier delivery mechanism along the article length such that the wedge-shaped lead element wedges intermediate the article and the support structure thereby raising the article and enabling the article to roll atop the plurality of support rollers as the barrier delivery mechanism is directed along the article length.

12. The disinfection method according to claim 11 comprising the step of adjusting a height of the barrier delivery mechanism before directing the barrier delivery mechanism toward the article so as to position the wedge-shaped lead element for horizontal insertion intermediate the article and the support structure.

13. The disinfection method according to claim 10, wherein the barrier delivery, containment apparatus is reconfigurable intermediate a vertical stowage configuration and a horizontal application configuration.

14. The disinfection method according to claim 13, wherein the plurality of support rollers are configured to rollably elevate the article within the gas-impermeable barrier when transitioning from the vertical stowage configuration to the horizontal application configuration.

15. The disinfection method according to claim 14, wherein the vertical stowage configuration is enabled by a vertically-oriented roller-support carriage and the horizontal application configuration is enabled by a horizontally-oriented roller-support carriage, the vertically-oriented roller support carriage and the horizontally-oriented roller-support carriage both comprising opposed roller-receiving tracks for rollably supporting the support rollers.

16. The disinfection method according to claim 15, wherein the barrier delivery, containment apparatus comprises opposed side rail assemblies stowable upon the vertically-oriented roller-support carriage when in the vertical stowage configuration, the opposed side rail assemblies being removable from the vertically-oriented roller support carriage and attachable to a lower end of the vertically-oriented roller-support carriage when reconfigured into the horizontal application configuration.

17. The disinfection method according to claim 16, wherein roller-receiving tracks of each side rail assembly are placed in-line with roller-receiving tracks of the vertically-oriented roller-support carriage thereby together providing L-shaped roller-receiving tracks.

18. The disinfection method according to claim 10, wherein the apparatus-treated air is treated by at least one of ozonating the air and heating the air.

* * * * *